US010937268B1

(12) United States Patent
Morad et al.

(10) Patent No.: US 10,937,268 B1
(45) Date of Patent: Mar. 2, 2021

(54) APPARATUS TO DISPENSE TWO SEPARATE PRODUCTS THROUGH A COIN-OPERATED SYSTEM

(71) Applicants: Fred I. Morad, Toluca Lake, CA (US); Robert A. Acosta, Norwalk, CA (US)

(72) Inventors: Fred I. Morad, Toluca Lake, CA (US); Robert A. Acosta, Norwalk, CA (US)

(73) Assignee: Worldwide Integrated Resources, Inc., Montebello, CA (US)

(*) Notice: Subject to any disclaimer, the term of this patent is extended or adjusted under 35 U.S.C. 154(b) by 0 days.

(21) Appl. No.: 16/664,922

(22) Filed: Oct. 27, 2019

(51) Int. Cl.
*G07F 11/04* (2006.01)
*G07F 5/02* (2006.01)
*G07F 11/22* (2006.01)
*A61F 13/551* (2006.01)

(52) U.S. Cl.
CPC ........ *G07F 11/045* (2013.01); *A61F 13/5519* (2013.01); *G07F 5/02* (2013.01); *G07F 11/22* (2013.01)

(58) Field of Classification Search
CPC .......... A61F 13/5519; G07F 1/06; G07F 5/02; G07F 11/22; G07F 11/045; G07F 11/62
See application file for complete search history.

(56) References Cited

U.S. PATENT DOCUMENTS

| 1,947,767 | A | * | 2/1934 | Gilchrist | G07F 1/046 194/327 |
| 3,265,177 | A | * | 8/1966 | Knickerbocker | G07F 11/16 194/247 |
| 3,397,764 | A | * | 8/1968 | Simjian | G07F 7/00 194/212 |
| 4,553,657 | A | * | 11/1985 | Kilmartin | G07F 1/06 194/213 |
| 4,986,524 | A | * | 1/1991 | Meintzer, Jr. | B65H 3/10 112/113 |
| 5,167,345 | A | * | 12/1992 | Bleeker | G07F 11/10 221/103 |
| 7,469,779 | B2 | * | 12/2008 | Horian | G07F 1/047 194/232 |
| 9,501,888 | B1 | * | 11/2016 | Morad | G07F 11/10 |
| 9,721,419 | B1 | * | 8/2017 | Morad | A61F 13/55185 |
| 9,779,574 | B1 | * | 10/2017 | Morad | G08B 21/18 |
| 10,062,236 | B2 | * | 8/2018 | Morad | A61F 13/55135 |
| 2003/0183645 | A1 | * | 10/2003 | Shin | G07F 9/105 221/133 |
| 2011/0000760 | A1 | * | 1/2011 | LaCroix-Toyne | G07F 5/00 194/350 |
| 2018/0025572 | A1 | * | 1/2018 | Morad | G07F 11/045 221/6 |
| 2018/0114396 | A1 | * | 4/2018 | Morad | G07F 11/04 |

* cited by examiner

*Primary Examiner* — Gene O Crawford
*Assistant Examiner* — Kelvin L Randall, Jr.

(57) ABSTRACT

A dispenser of feminine pads and tampons activated by a touch sensor. The touch of a person's hand will close an electronic circuit causing a motor to rotate. The motor is attached to a shaft which rotates. The shaft retains a feminine product dispenser. The feminine product dispenser transports a feminine napkin or tampon to a retrieval tray. The improved design enables the sanitary napkin rack and tampon rack to be adjacent to each other, thereby reducing the width requirements for the cabinet housing the racks. The activation by touch screen significantly improves the selection and dispensing of the desired feminine napkin product and tampon product.

17 Claims, 22 Drawing Sheets

APPARATUS TO DISPENSE TWO SEPARATE PRODUCTS THROUGH A COIN-OPERATED SYSTEM

BACKGROUND OF THE INVENTION

1. Field of the Invention

The present invention relates to the field of vending machines which are used to dispense products such as feminine hygiene products including feminine pads and tampons.

2. Description of the Prior Art

The closest prior art of which the present inventors are aware include the following issued United States Patents:

1. U.S. Pat. No. 9,501,888 for "Vending Machine for Retaining and Dispensing Feminine Hygiene Products Through a Novel Coin Operating Apparatus" issued on Nov. 22, 2016, where two of the inventors were Fred I. Morad and Robert A. Acosta;

2. U.S. Pat. No. 9,721,419 for "Vending Machine for Retaining and Dispensing Feminine Hygiene Products Through a Novel Coin Operating Apparatus" issued on Aug. 1, 2017, where two of the inventors were Fred I. Morad and Robert A. Acosta;

3. U.S. Pat. No. 9,779,574 for "Vending Machine for Retaining and Dispensing Hygiene Products Through A Novel Coin Operating Apparatus" issued on Oct. 3, 2017, where two of the inventors were Fred I. Morad and Robert A. Acosta;

4. U.S. Pat. No. 10,062,236 for "Vending Machine for Retaining and Dispensing Products" issued on Aug. 28, 2018, where two of the inventors were Fred I. Morad and Robert A. Acosta;

To the best of the present inventors' knowledge, there is no issued patent or published patent application which identically discloses or makes obvious the present invention.

SUMMARY OF THE INVENTION

The present invention relates to vending machines that dispense two separate products selected by placing at least one coin in a designated coin slot. Specifically, the invention relates to vending machines that dispense feminine hygiene products without requiring any physical activity such as turning a knob or other physical apparatus to dispense the feminine hygiene products from the vending a machine. The invention further relates to vending machines that dispense feminine hygiene products that do not require activation by a motion of a body part such as waiving a hand in front of a motion sensor to enable a product to be dispensed from the vending machine.

The present invention is a vending machine which contains two rows of products to be separately dispensed from a vending machine upon depositing the required amount of coins in a slot designated for purchasing a specific one of the two products. By way of example, the two products are feminine hygiene products adjacent one another, with sanitary pads (sanitary napkins) in one row and tampons in a second row.

The novel feature of the present invention is the insertion of a required type of coin or coins and a required number of the same coin into a slot designated for purchasing a specific product. The unique feature of this invention is facilitating the purchase of a specific product by only requiring the insertion of one or more designated coins in a designated slot without requiring a purchaser to engage in a physical activity such as rotating a knob, pushing a button or requiring a physical motion such as waiving a hand in front of a motion sensor. Therefore, the present invention eliminates physical exertion such as rotating a knob which might be difficult for for elderly users. The present invention also eliminates a requirement for a purchaser to engage in a physical activity such as waiving a hand in front of a motion sensor to activate a product being dispensed. In addition, such a purchase of a product can only occur if at least one correct coin is deposited in a correct coin slot. The present invention therefore eliminates a purchaser want only emptying a quantity of products from a machine where only an activity such as waiving a hand and no money was required for a purchase of a product from the vending machine. With the present invention, a product is dispensed only after money is deposited. The present invention also eliminates a time delay between products being dispensed.

The unique coin system of the present invention includes three operating plates affixed to each other in a horizontal row behind the back surface of a front cover of the vending machine. By way of example, the vending machine is programmed to accept one quarter or two quarters for a purchase. The rearmost plate addresses a problem if an incorrect coin, such as a penny, a nickle or a dime is inserted in the coin slot. The rearmost plate prevents the incorrect coin from entering a coin receipt slot and instead causes the incorrect coin to fall into an opening and return the incorrect coin to a retrieval slot so the user can retrieve the incorrect coin.

Second, the vending machine is programmed to provide an advisory signal if the machine is out of a specific product. A flashing light adjacent a coin deposit slot advises a user that the machine is out of the product for which a coin is deposited in the slot adjacent the flashing signal. If a person deposits a correct coin when the vending machine is out of the product, the coin will fall straight down between the rearmost plate and a middle plate and fall into a coin retrieval tray.

If a machine still has a product for sale and the purchaser inserts the correct number of correct coin or coins in a correct coin slot, the machine causes the coin or coins to fall into a locked coin box and the machine is programmed to dispense he product into a retrieval slot. The first or third plate provides the activation of causing the coin to fall into a locked coin box and causing the vending machine to dispense the correct product.

The product retaining rails and dispensing apparatus are similar to product retaining rails and dispensing apparatus disclosed in a previous patent by the same inventors as identified in the description of prior art section in this application. Each row of each of the products are aligned in rails, one above the other within the row. There is a weight on top of each row of the products to create a downward force to enable the next successive product to be placed in condition for dispensing after the lowermost product has been dispensed. The rails have a rear surface and a pair of side rails which envelope the specific packaging in which each respective feminine hygiene product is retained. There is an aligned horizontal dispensing platform on which the lowest feminine hygiene product is retained with opposite distribution arms which assist in dispensing the retained lowermost feminine hygiene product and assist in receiving the next lowermost feminine hygiene product. Each pair of distribution arms receives the lowermost feminine napkin or tampon and rotates in one direction by about one-hundred and eighty (180) degrees to enable the product to be dispensed into a retrieving tray. The dispensing arms have duplicate distribution arms so that the next lowermost product falls into the upper distribution arm. When the machine is activated to dispense the next product, the dispensing arm rotates by another one-hundred and eighty (180) degrees to dispense the next product into a product retrieving tray. Therefore, the dispensing arm rotates a total of three-hundred and sixty (360) degrees in the same direction, with a product distributed upon a one-hundred eighty degree rotation. In the prior art, the rotation of a dispensing arm was only forty-five (45) degrees which required a complicated apparatus to push a product off a dispensing arm and into a retrieval tray. With a one-hundred eighty degree rotation, the product falls off the dispensing arm and into the retrieval tray without requiring an apparatus to push the product off the dispensing arm.

By way of example, the feminine napkins are retained in a rail in a vertically aligned row of products with a weight thereon and a magnet on top of the weight. From a view looking inside the cabinet (the door opens to the left), and facing the dispensing module, the feminine napkins are on the left and the tampons are on the right. All components will be identified by these positions.

The components that are mounted to the back of the door such as LED lights, "coin module" and all electrical switches and solenoids are referred to as left and right, napkin and tampon respectively. Therefore, in a view looking at the interior with the door open, what is on the left is feminine napkins and what is on the right is tampons. The components are a motor attached to a shaft, a microswitch, an LED light, and a reed switch triggered by a magnet within or on top of a weight resting on top of a column of products.

When the supply of feminine napkins is exhausted and there are no more feminine napkins in the row, the magnet on top of a weight at the top of the feminine napkin column is proximate the left reed switch or feminine napkin reed switch which causes a warning light to blink on and off. As shown in the FIG. 1 which will be described, the right warning light or right feminine napkin warning light is hardwired by two wire leads to female connectors on the motherboard. Therefore, when the rail retaining the column of feminine napkins is out of feminine napkins, when the magnet on top of the weight is lowered to be proximate with the reed switch at the bottom of the feminine napkin column, then the light will blink on and off and is visible through an opening in the front door adjacent to the coin slot for purchase of feminine napkins. The motherboard also sends a signal to the coin plate assembly to open a trap door and to enable the coin to fall into an opening and fall into a return slot.

When the supply of tampons is exhausted and there are no more tampons in the row, the magnet within or on top of a weight at the top of the column of tampons is proximate the right reed switch or tampon reed switch which causes a warning light to blink on and off. As shown in the FIG. 1 which will be described, the left warning light or left tampon warning light is hardwired by two wire leads to female connectors on the motherboard. Therefore, when the rail retaining the column of tampons is out of tampons, when the magnet on top of the weight is lowered to be proximate with the reed switch at the bottom of the tampon column, the light will blink on and off and is visible through an opening in the front door adjacent to the coin slot for the purchase of tampons. The motherboard also sends a signal to the coin plate assembly to open a trap door and to enable the coin to fall into an opening and fall into a return slot.

Upon activation, the feminine napkin motor shaft is caused to rotate one-hundred eighty (180) degrees which in turn is connected directly to the dispensing cradle. For every one-hundred eighty (180) degree rotation, the feminine napkin dispensing cradle will dispense one product per coin or coins. This unit does not use a crank or crank arms or a flywheel.

Upon activation, the tampon motor shaft is caused to rotate one-hundred eighty (180) degrees which in turn is connected directly to the dispensing cradle. For every one-hundred eighty (180) degree rotation, the tampon dispensing cradle will dispense one product per coin or coins. This unit does not use a crank or crank arms or a flywheel.

With respect to the feminine napkins, the feminine napkin motor or left motor is hardwired by two wire leads to the female connectors on the motherboard. A left microswitch or feminine napkin microswitch is hardwired by two wire leads connected to the motherboard. When a tip on the dispensing cradle touches the microswitch, the motor stops after the one hundred eighty degree rotation.

With respect to the tampons, the tampon motor or right motor is hardwired by two wire leads to the female connectors on the motherboard. A right microswitch or tampon microswitch is hardwired by two wire leads connected to the motherboard. When a tip on the dispensing cradle touches the microswitch, the motor stops after the one hundred eighty degree rotation.

The present invention is preferably housed in a plastic or other comparable container with a cover made of different material and preferably opaque. It is also within the spirit and scope of the present invention for the vending machine cabinet to be made of metal.

Further novel features and other objects of the present invention will become apparent from the following detailed description and discussion.

DETAILED DESCRIPTION OF EMBODIMENTS OF THE PRESENT INVENTION

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention.

Figure 1:
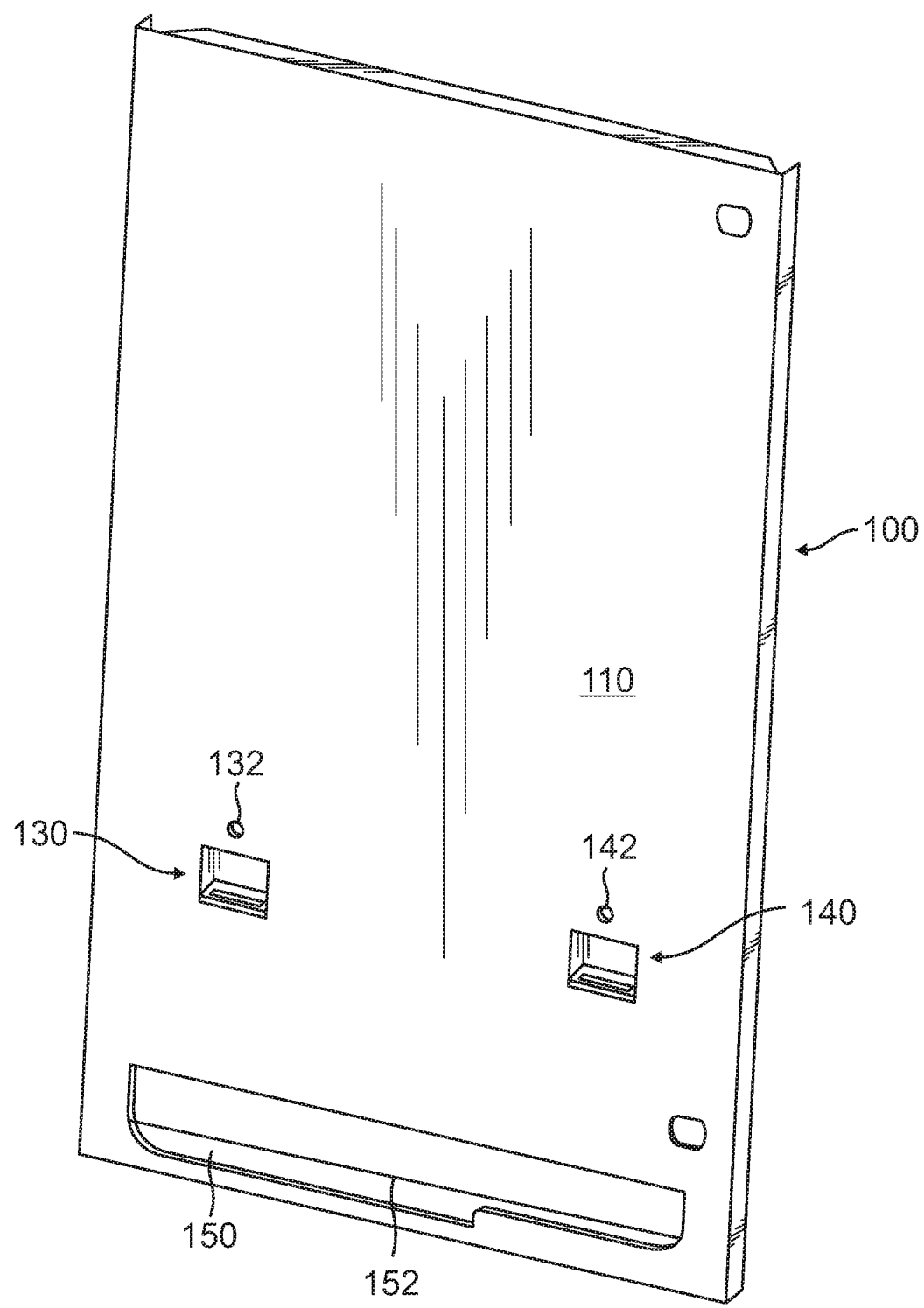
FIG. 1 is a front perspective view of the front door of the present invention coin-operated product dispensing machine, with the first product coin deposit slot on the right and the second product coin deposit slot on the left.

Referring to FIG. 1, there is illustrated a front perspective view of the front surface 110 of the front cabinet door 100 of the present invention coin-operated product dispensing machine. The front cabinet door 100 includes a first or left coin deposit slot 130, a first or left opening 132 for a light to indicate that the vending machine is out of a first product, a right or second coin deposit slot 140 and a second or right opening 142 for a light to indicate that the vending machine is out of the second product. The dispensing machine 10 is programmed to accept either one quarter or two quarters for a purchase of a product. The front cabinet door 100 also includes a retrieval opening 150 leading to a retrieval plate 152 through which a purchased product is retrieved, through which the deposited quarter or quarters is returned if the dispensing machine is out of the product sought to be purchased, or a return of money if an incorrect coin such as a penny, nickle or dime is inserted into either first coin deposit slot 130 or second coin deposit slot 140.

Figure 2:
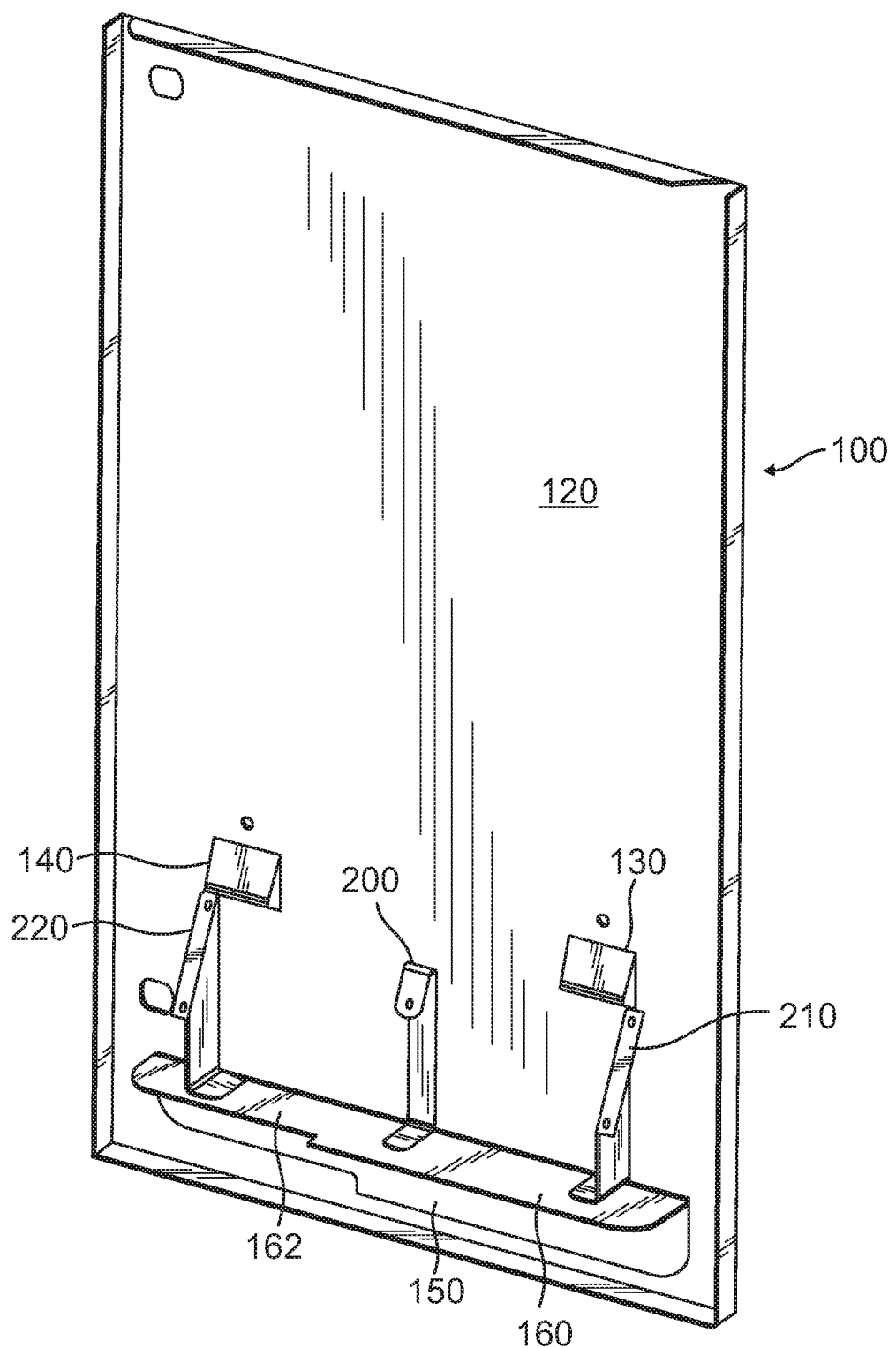
FIG. 2 is a rear perspective view of the back of the front cabinet door with the coin deposit slots aligned in reverse with the coin deposit slots on the front surface of the front door, also illustrating a horizontal separation wall.

Referring to FIG. 2, there is illustrated a rear perspective view of the back surface 120 of the front cabinet door 100. Also illustrated is the back of the first now on the right coin deposit slot 130 and the back of the second now of the left coin deposit slot 140. Since FIG. 2 is a view from the back, the coin deposit slots are oppositely oriented from the front view. A horizontal separation wall 160 separates the first or right coin deposit slot 130 and the second or left coin deposit slot 140 from the retrieval opening 150. The separation wall 160 is supported against the back surface 120 of front cabinet door 100 by a central mounting bracket 200, a right mounting bracket 210 and a left mounting bracket 220.

Figure 3:
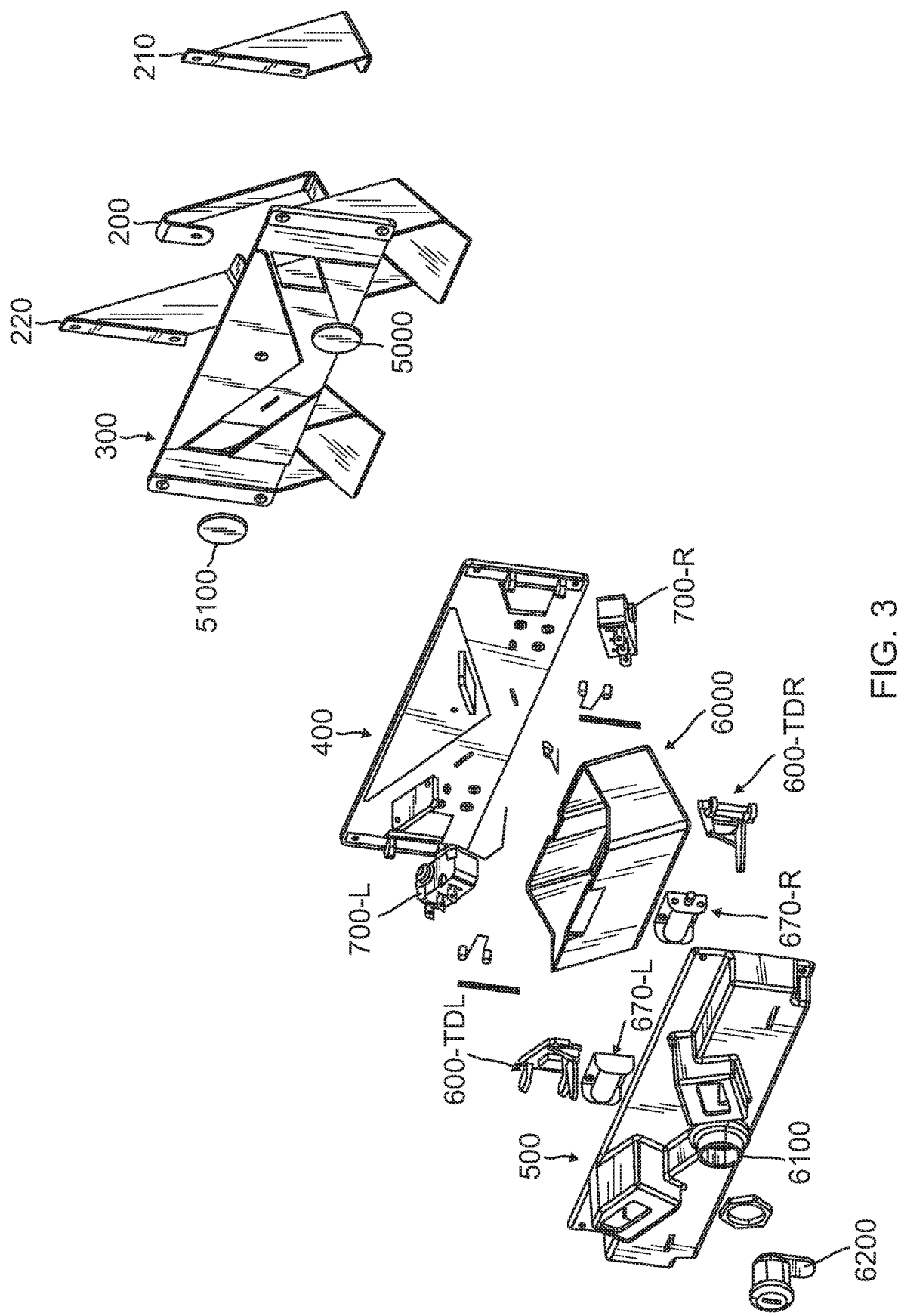
FIG. 3 is an exploded view of back plate, middle plate and front plate of the coin activation members which are a key portion of the innovation of the present invention.

A key innovation of the present invention dispensing apparatus are three operation plates. Referring to FIG. 3, there is illustrated an exploded view of the three operation plates and other components which are a major portion of the coin-operated vending machine of the present invention. The parts as numbered in FIG. 3 are described in succeeding paragraphs.

Figure 4:
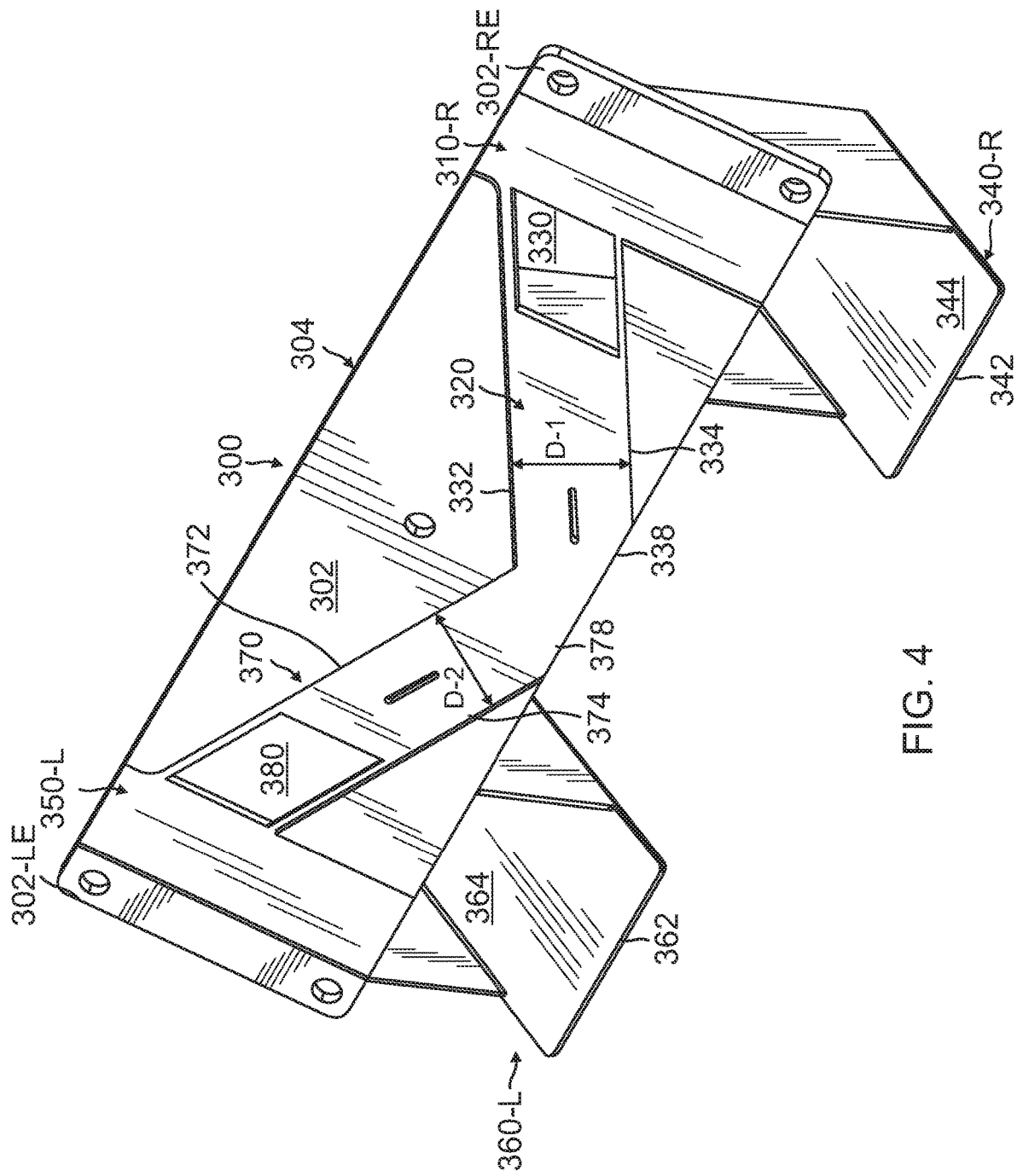
FIG. 4 is a front view of the back plate including a first transverse slope to return incorrectly deposited coins, a first or right coin slide slope, a second or left transverse slope to return incorrectly deposited coins and a second or left coin slide slope.

Referring to FIG. 4, there is illustrated a front view of the back plate 300. The rear surface 304 of the back plate 300 faces the back surface 120 of front cabinet door 100. The back plate 300 also includes a front surface 302. The back plate 300 includes a first or right transverse slope 310-R. If an improper coin such as a penny, nickle or dime is inserted into first or right coin deposit slot 130 (as identified from the rear surface 120), the coin is guided along first or right transverse slope 310-R to first or right coin return plate 340-R which causes the improperly inserted coin to fall into the retrieval tray 152 to be retrieved by the person who inserted the wrong coin. If a proper coin such as a quarter is inserted into first or right coin deposit slot 130, the quarter is guided to the first or right coin slide slope 320 to a first or right portion of a central end 338, with the first or right coin slide slope 330 having a first or right upper wall 332 and a first or right lower wall 334 separated by a distance "D-1" sized to receive a quarter. The first or right trap door opening 330 is aligned with a first or right coin return plate 340-R. The route the quarter travels will be described after all three operating plates are described.

Similarly, the back plate 300 includes a second or left transverse slope 350-L. If an improper coin such as a penny, nickle or dime is inserted into second or left coin deposit slot 140 ((as identified from the rear surface 120), the coin is guided along second or left transverse slope 350-L to second or left coin return plate 360-L which causes the improperly inserted coin to fall into the retrieval tray 152 to be retrieved by the person who inserted the wrong coin. If a proper coin such as a quarter is inserted into second or left coin deposit slot 140, the quarter is guided to the second or left coin slide slope 370 to a second or left portion of a central end 378, with the second or left coin slide slope 370 having a second or left upper wall 372 and a second or left lower wall 374 separated by a distance "D-2" sized to receive a quarter. The second or left trap door opening 380 is aligned with the second or left coin return plate 360-L. The route the quarter travels will be described after all three operating plates are described.

The back plate is retained by the first or right mounting bracket 210, and the second or left mounting bracket 220, with both the bottom surface 342 of the first or right coin return plate 340-R and the bottom surface 362 or second or left coin return plate 360-L. affixed to separation plate 160.

Slope central ends 338 and 378 meet at the effective width-wise center of back plate 300.

In operation, the bottom surface 342 of first or right coin return plate 340-R is affixed to upper surface 162 of separation wall 160 and bottom surface 362 of second or left coin return plate 360-L is also affixed to upper surface 162 of separation wall 160. If an incorrect size coin such as a penny, nickle or dime is inserted into first or right coin slot opening 130, it falls down right transverse return slope 310-R and falls into the top surface 344 of first or right coin return plate 340-R and falls into retrieval tray 152. Similarly, if an incorrect size coin such as a penny, nickle or dime is inserted into second or left coin slot opening 140, it falls down into the top surface 364 of second or left coin return plate 360-L and falls into retrieval opening 150.

Figure 5:
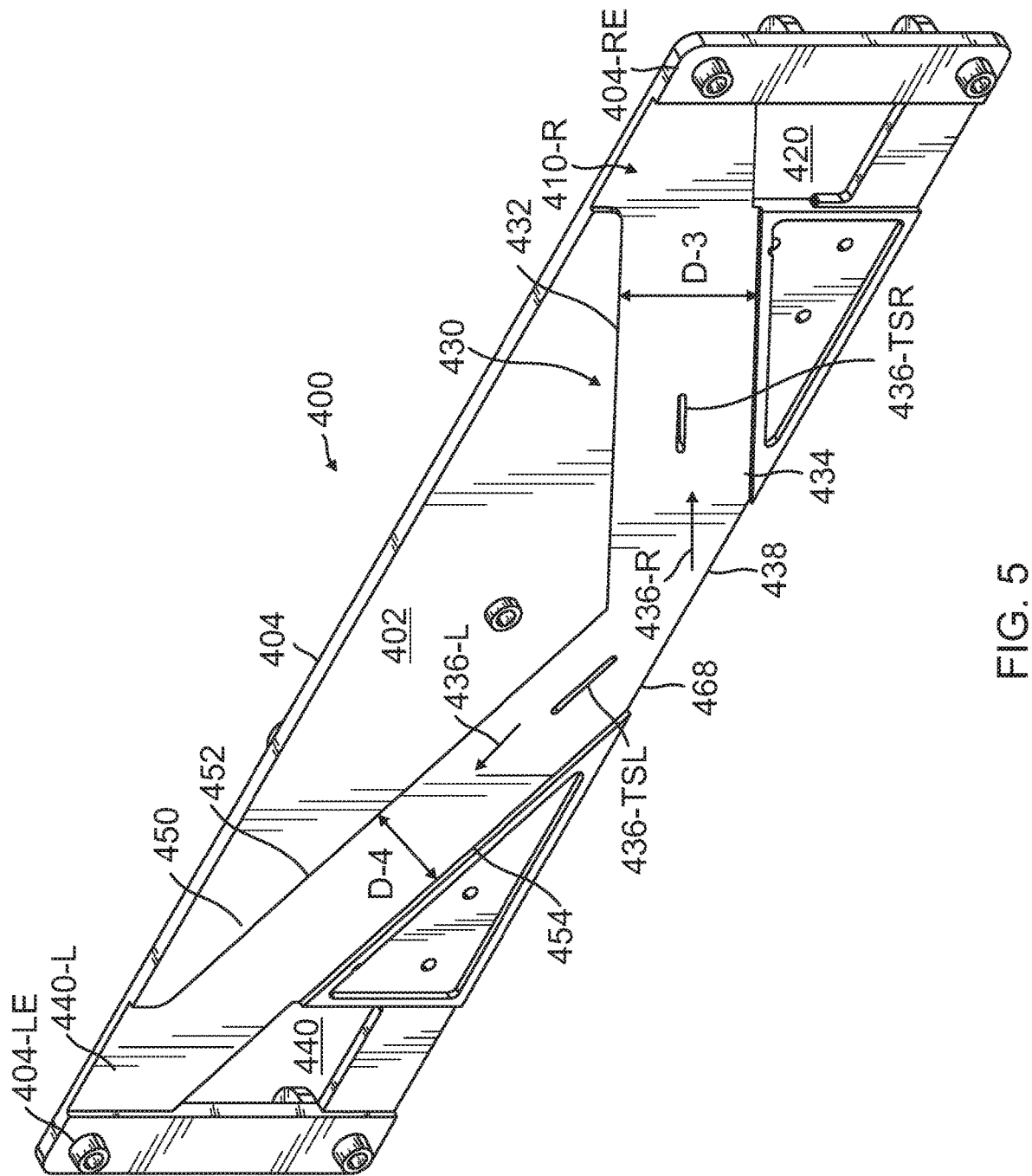
FIG. 5 is a front view of the middle plate including a first or right coin slide slope, a first or right trap door opening to return coins if the vending machine is out of the first product, a second or left coin slide slope, and a second or left trap door opening to return coins if the vending machine is out of the second product.

Referring to FIG. 5, there is illustrated a front perspective view of the middle plate 400 which includes a back surface 404 facing the front surface 302 of back plate 300. A first or right rear end 404-RE if affixed to a first or right front end 302-RE of back plate 300 and a second or left rear end 404-LE is affixed to a second or left front end 302-LE of back plate 300.

The front surface 402 of middle plate 400 includes a first or right transverse slope 410-R in line with a first or right trap door opening 420 and offset to a first or right slide slope 430 having an upper wall 432 and a lower wall 434 separated by a distance "D-3" and terminating in a first or right portion of a central end 438.

Similarly, the front surface 402 of middle plate 400 includes a second or left transverse slope 440-L in line with a second or left trap door opening 440 and offset to a second or left slide slope 450 having an upper wall 452 and a lower wall 454 separated by a distance "D-4" and terminating in a second or left portion of a central end 468.

Figure 6:
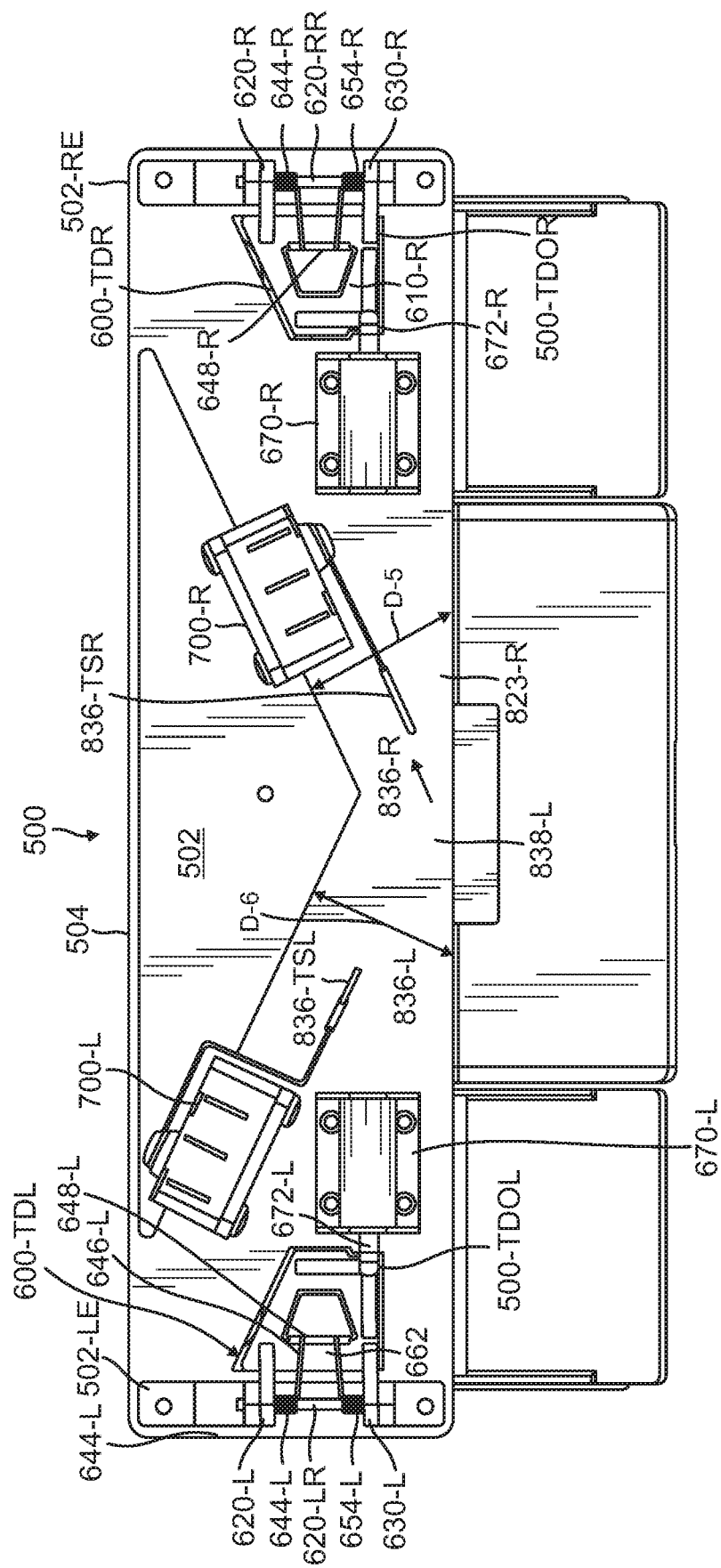
FIG. 6 is a front view of the front plate illustrating the coin operating components of the invention when the correct coin or coins is inserted into the correct slot with an opening for the coin or coins to fall into a coin box and the electric mechanism to have the selected product dispensed into a product retrieval tray.

Referring to FIG. 6, there is illustrated a front view of the third or rearmost plate, also called the front plate 500 which is illustrate from its front surface 502, with its back surface 504 facing the front surface 402 of middle plate 400. A first or right front end 502-RE of front plate 500 is affixed to the first or right rear end 404-RE of middle plate 400. A second or left front end 502-LE of front plate 500 Is affixed to second or left rear end 404-LE of middle plate 400.

Figure 6A:
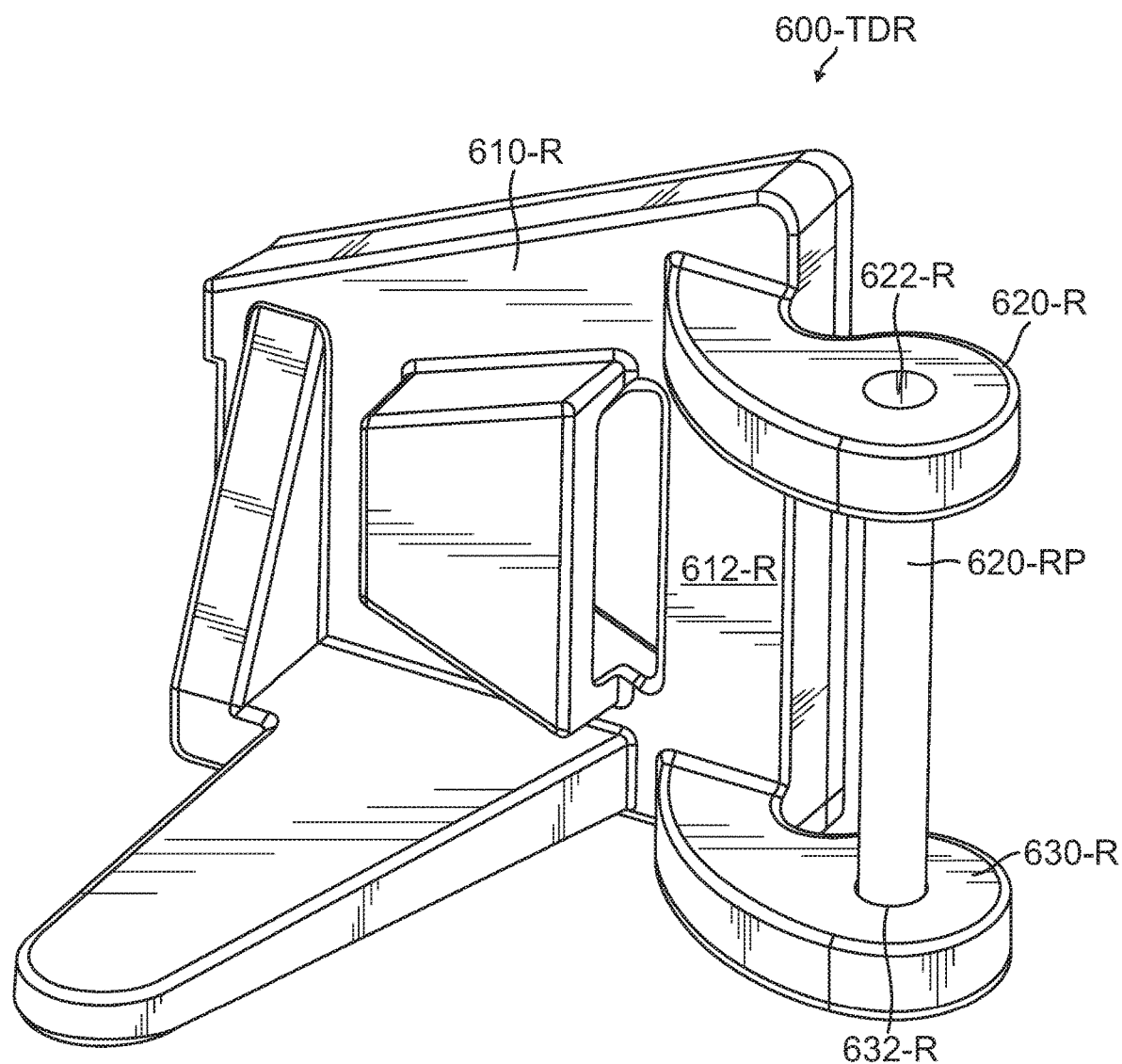
FIG. 6A is a perspective view of the first or right trap door and rotation arms.
Figure 6B:
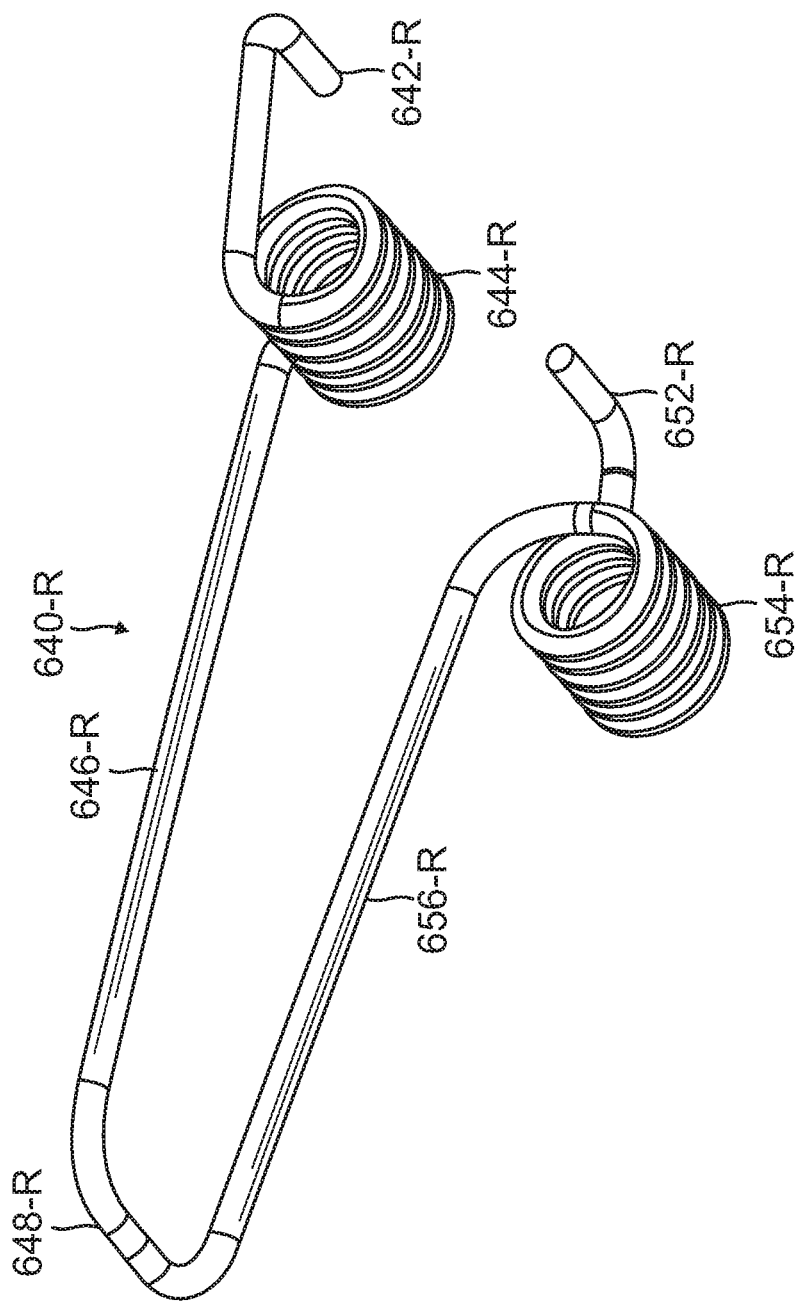
FIG. 6B is a perspective view of the first or right return spring.

The front plate 500 includes several operating components illustrated in FIG. 6 and separately described in greater detail in the following figures. A spring loaded first or right trap door 600-TDR is illustrated in FIG. 6 and is separately illustrated by itself in FIG. 6A and includes a first or right plate 610-R with a rear surface 612-R which includes a pair of spaced part arms including a first arm 620-R with a central opening 622-R and a spaced apart second arm 630-R with a central opening 632-R. Referring to FIG. 6B, there is illustrated a first or right return spring 640-R with a first bent post 642-R inserted into central opening 622-R of first arm 620-R and a second bent post 652-R inserted into central opening 632-R of second arm 630-R. Each bent post 642-R and 652-R respectively terminating in a first spring coil 644-R and second spring coil 654-R wrapped around post 620-RP and which extend to respective interior shafts 646-R and 656-R which join at an interior transverse shaft 648-R. The interior transverse shaft 648-R is supported on a first or right spring plate 610-R as illustrated in FIG. 6. With no restraint, the first spring coil 644-R and the second spring coil 654-R would exert a counterclockwise force on first or right plate 610-R, causing the plate 610-R to rotate away from the surface 502 of third plate 500 thereby exposing a first front plate or right traps door opening 500-TDOR which is aligned with first or right trap door opening 420 of middle plate 400.

Figure 6C:
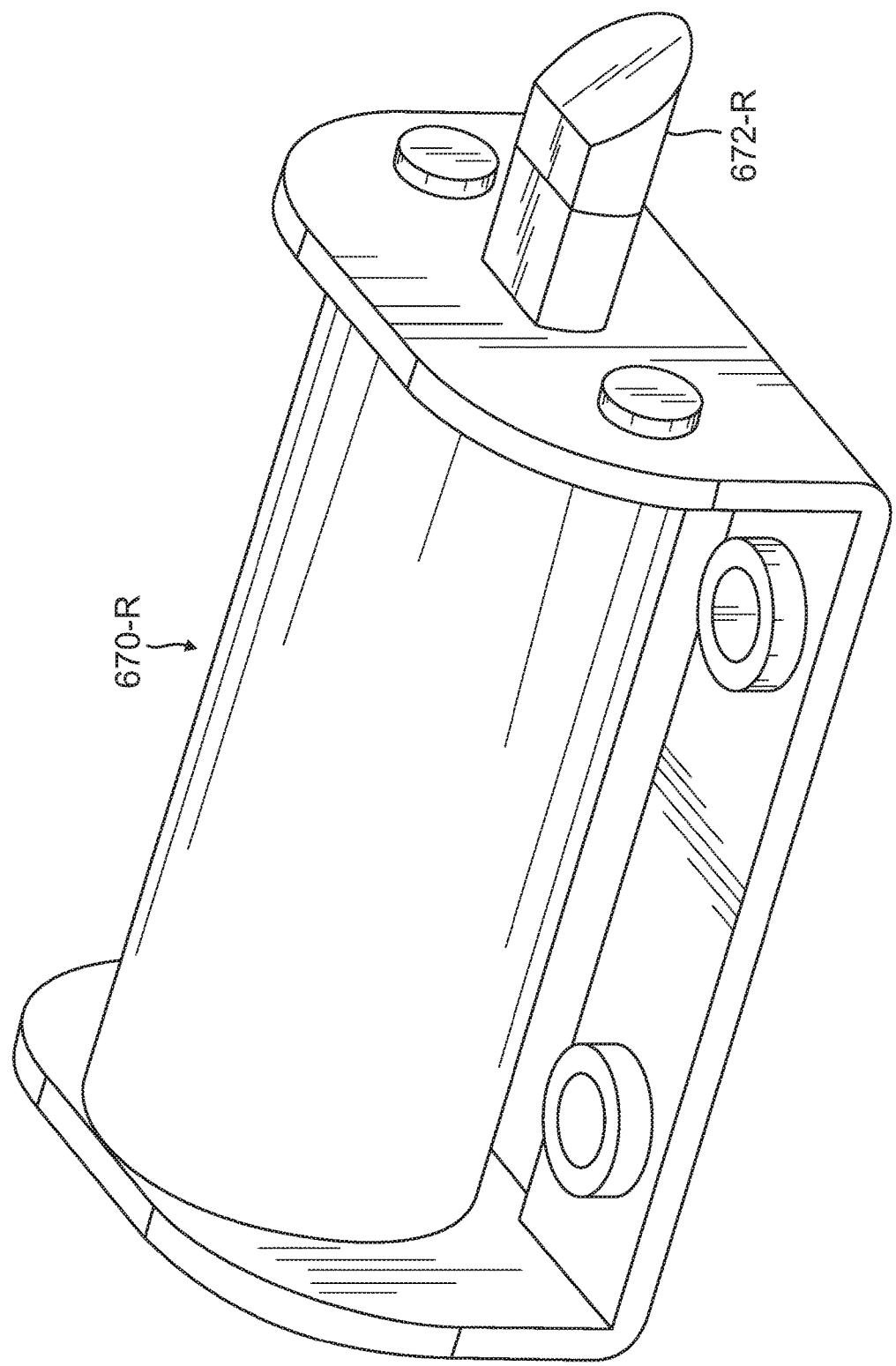
FIG. 6C is a perspective view of the first or right solenoid valve.

Referring to FIGS. 6 and 6C, preventing the coil spring action is first or right solenoid 670-R affixed to front surface 502 of front plate 500. The first or right solenoid 670-R includes a retaining pin 672-R. When the first or right solenoid 670-R is not activated, the retaining pin 672-R is pressed against plate 610-R and prevents the spring action rotation of plate 610-R. When activated, the retaining pin 672-R is retracted back into solenoid 670-R and the first or right spring loaded first or right plate 610-R of first or right trap door 600-TDR rotates away from front surface 502 exposing the trap door opening 600-TDOR and previously closed and now open trap door opening 420 of middle plate 400.

Figure 6D:
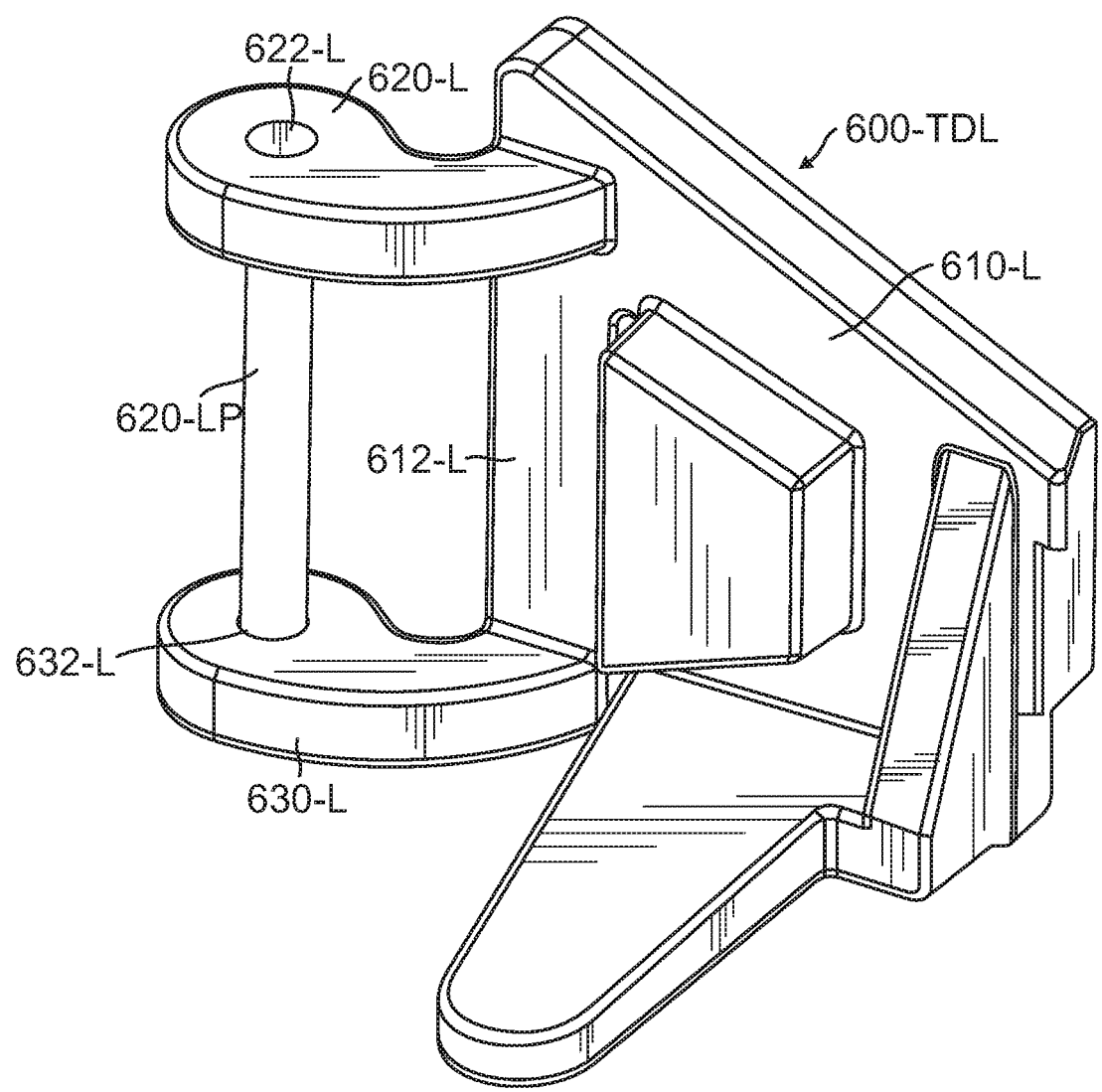
FIG. 6D is a perspective view of the second or left trap door and rotation arms.
Figure 6E:
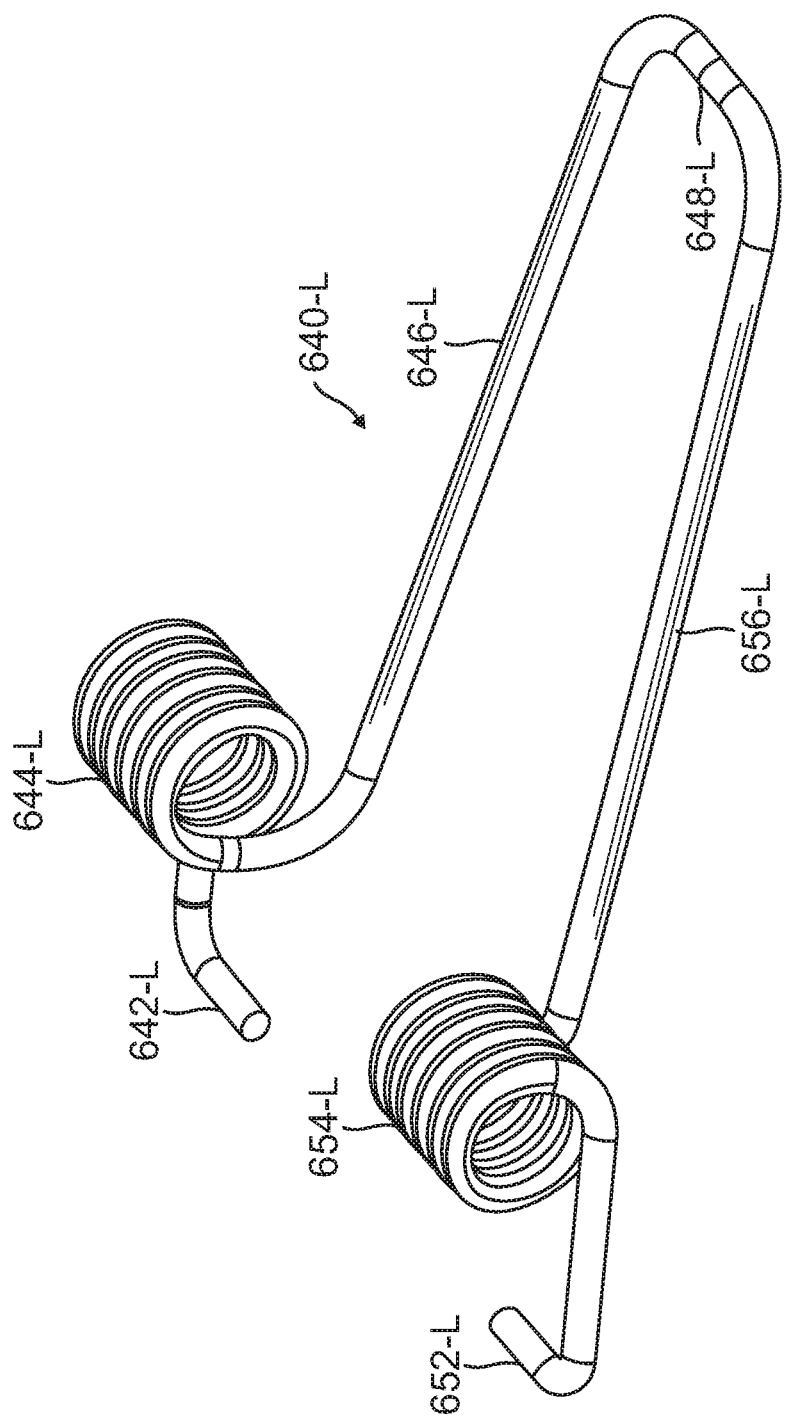
FIG. 6E is a perspective view of the second or left return spring.
Figure 6F:
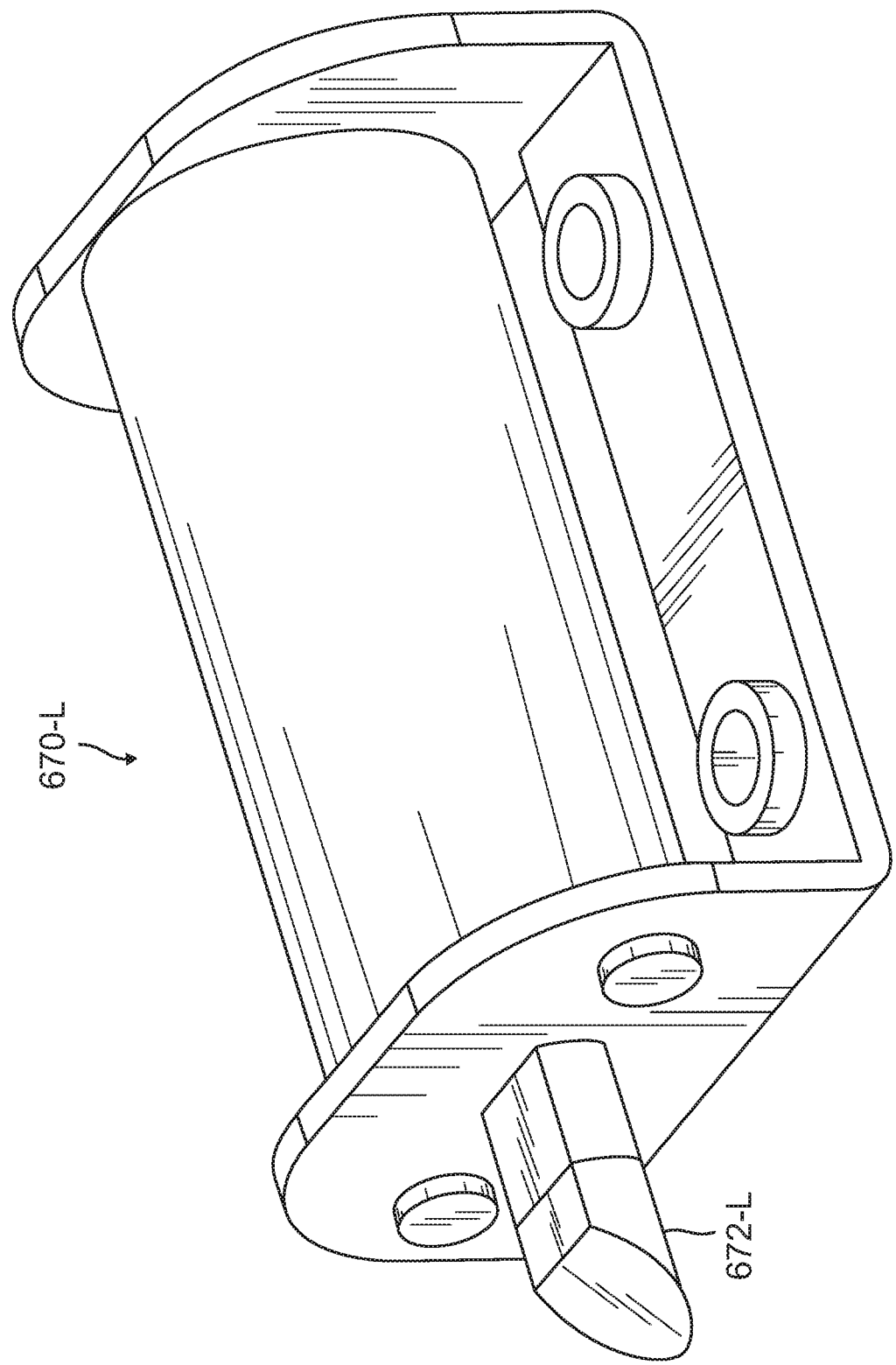
FIG. 6F is a perspective view of the second or right right solenoid valve.

Similarly, a spring loaded second or left trap door 600-TDL is illustrated in FIG. 6 and is separately illustrated by itself in FIG. 6D and includes a second or left plate 610-L with a left surface 612-L which includes a pair of spaced part arms including a first arm 620-L with a central opening 622-L and a spaced apart second arm 630-L with a central opening 632-L. Referring to FIG. 6E, there is illustrated a second or left return spring 640-L with a first bent post 642-L inserted into central opening 622-L of first arm 620-L and a second bent post 652-L inserted into central opening 632-L of second arm 630-L. Each bent post 642-L and 652-L respectively terminates in a first spring coil 644-L and second spring coil 654-L wrapped around left post 620-LP and which extend to respective interior shafts 646-L and 656-L which join at an interior transverse shaft 648-L. The interior transverse shaft 648-L is supported on a second or left spring plate 610-L as illustrated in FIG. 6. With no restraint, the first spring coil 644-L and the second spring coil 654-L would exert a clockwise force on second or left plate 610-L, causing the plate 610-L to rotate away from the surface 502 of third plate 500 thereby exposing a second or left trap door opening 500-TDOL which is aligned with second or left trap door opening 450 of middle plate 400.

Figure 7:
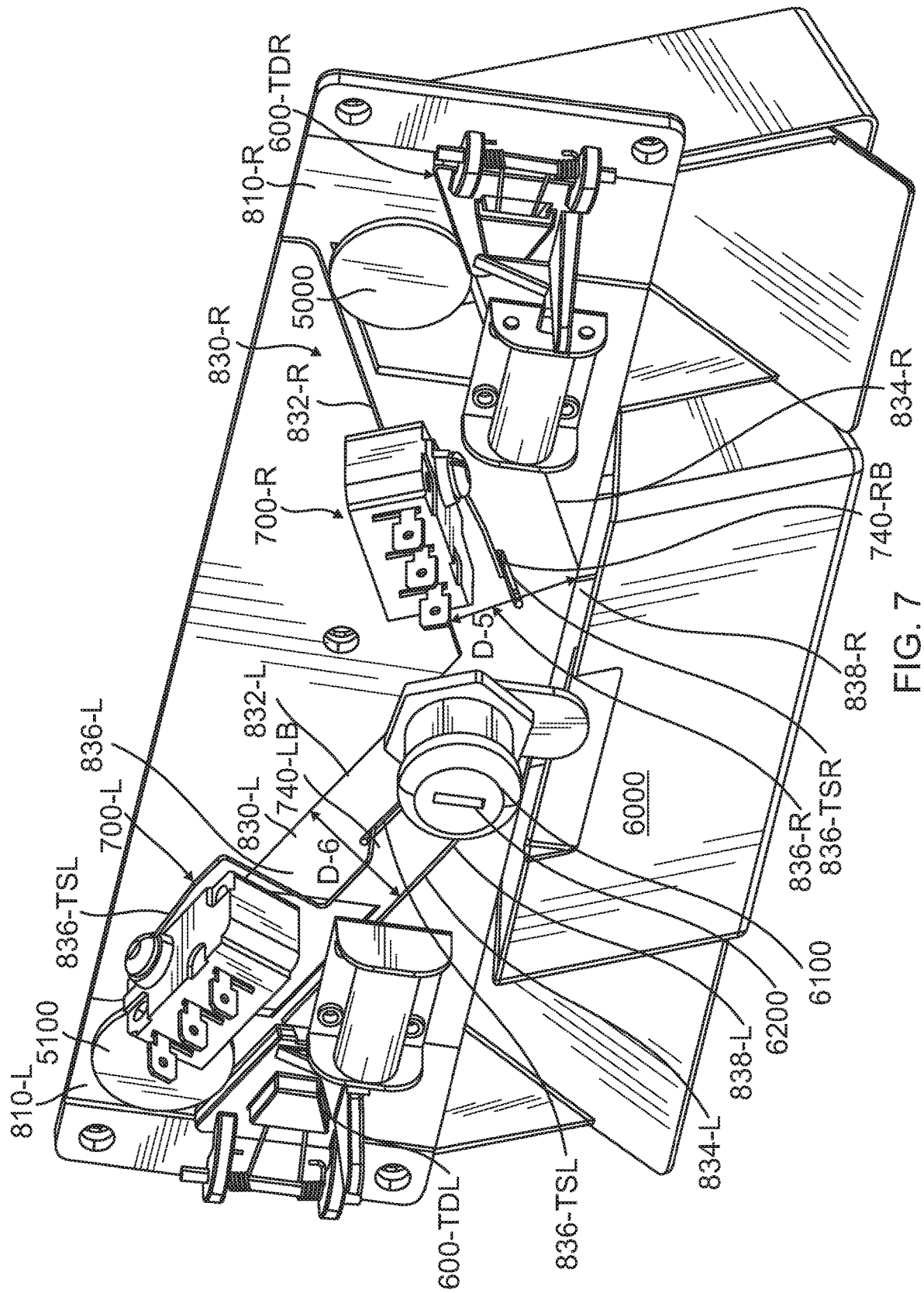
FIG. 7 is a front view of the front plate in a closed condition and the coin box locked.
Figure 8A:
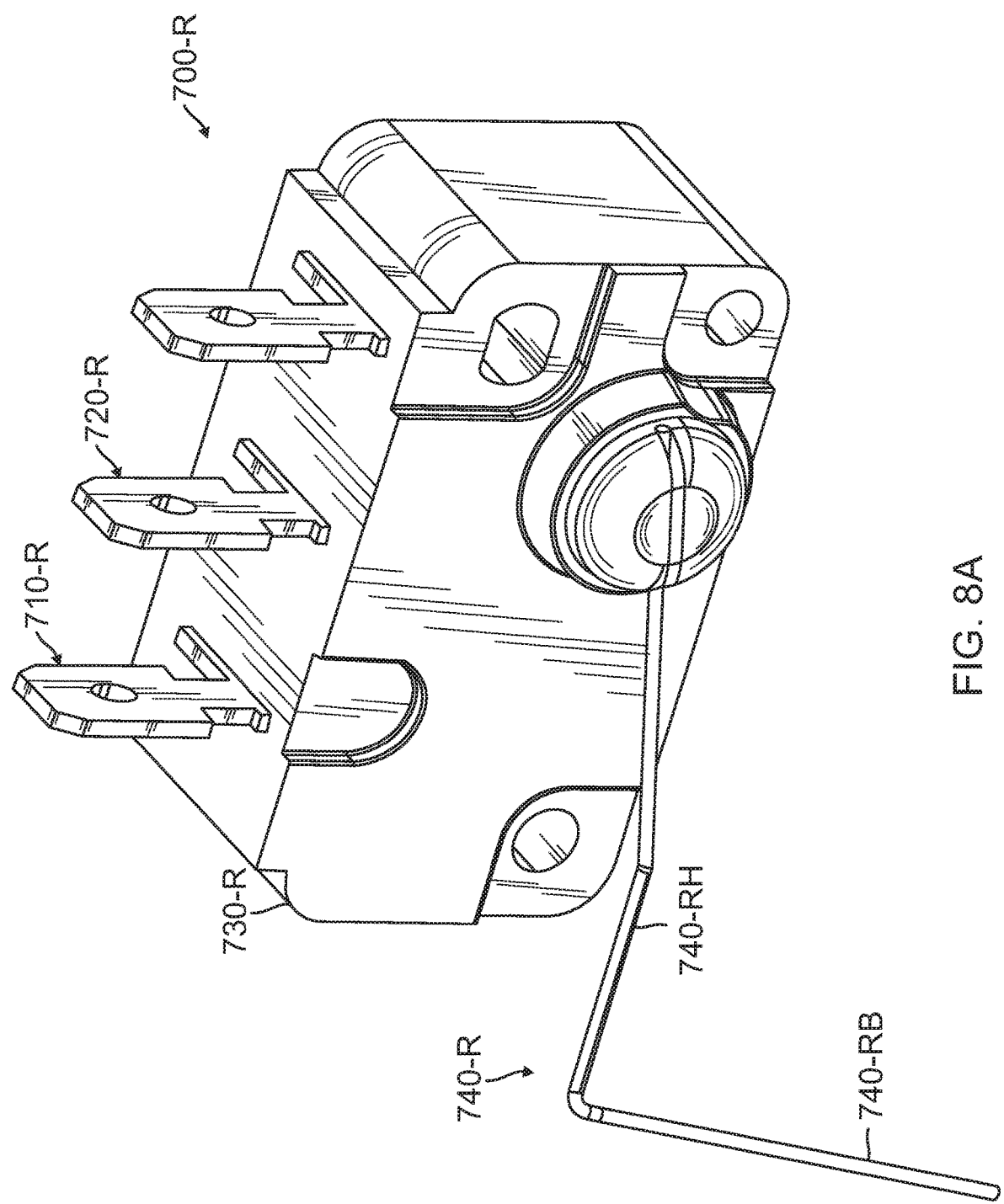
FIG. 8A is a perspective view of a right trigger switch and its components.
Figure 8B:
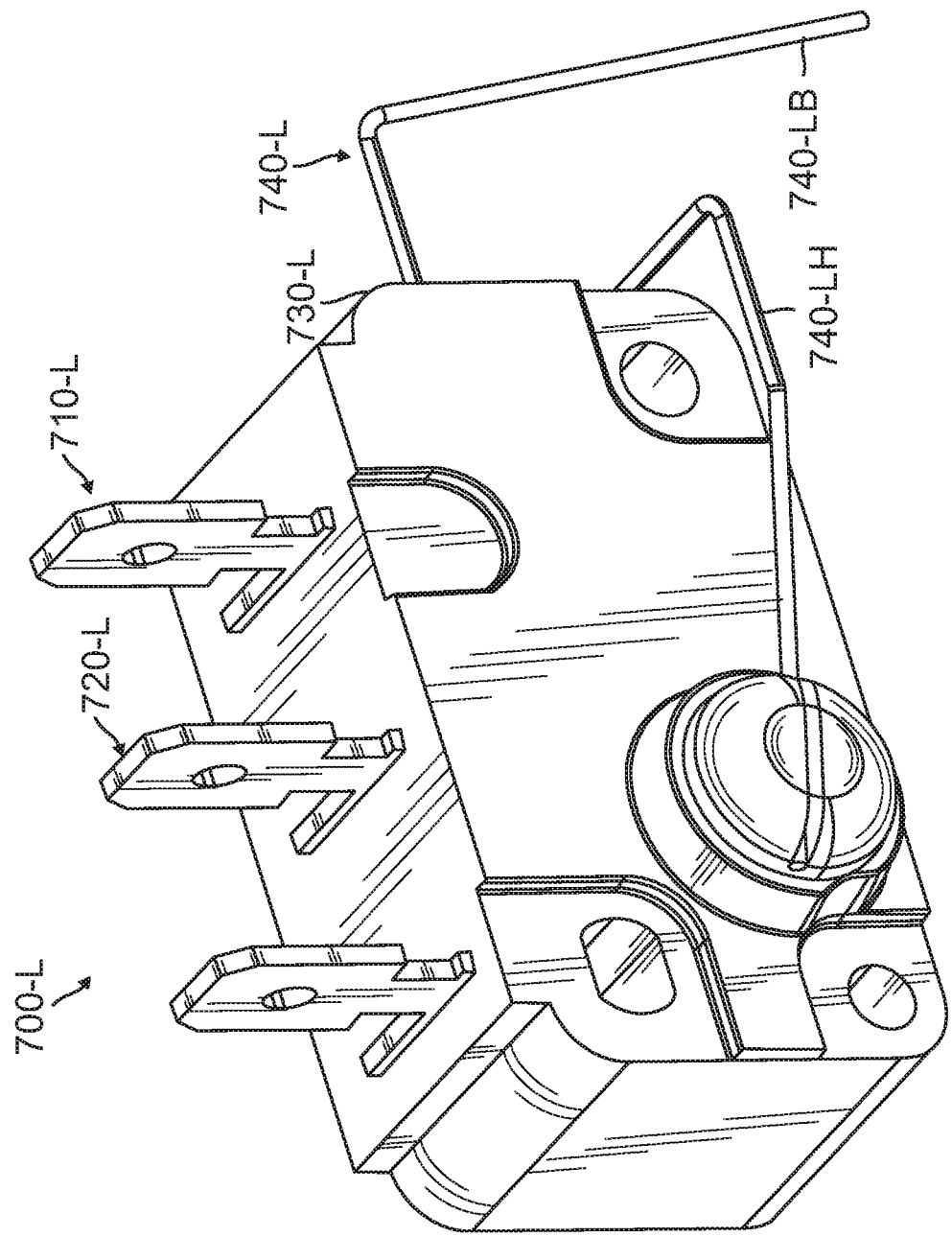
FIG. 8B is a perspective view of a left trigger switch and its components.

Further referring to FIG. 6, there is illustrated a front view of the front plate 500 with a top perspective view of the first or right trigger switch 700-R and the second or left trigger switch 700-L. Referring to FIG. 7, there is illustrated a front perspective view of components of the front plate 500 including the top and side perspective view of the first or right trigger switch 700-R and the second or left trigger switch 700-L. Referring to FIG. 8A, there is illustrated a front, top and side perspective view of the first or right trigger switch 700-R. Referring to FIG. 8B, there is illustrated a front, top and side perspective of the second or left trigger switch 700-L. The two trigger switches, 700-R and 700-L are mirror images of each other.

Referring to FIGS. 6, 7 and 8A, the right trigger switch 700-R inches three vertical posts, a left post 710-R which is a "hot" wire connection and middle post 720-R which is neutral or ground. The third post is not used. The internal activation mechanism is within housing 730-R and is activated by a bent trigger shaft 740-R which includes a horizontal portion 740-RH and a bent portion 740-RB.

Referring to FIG. 7, the front surface 502 of front plate 500 includes a first or right transverse slope 810-R in line with the first or right trap door 610-TDR and offset to a first or right slide slope 830-R having an upper wall 832-R and a lower wall 834-R separated by a distance "D-5" and terminating in a first or right portion of a central end 838-R. A first or right trigger switch slot 836-TSR is centered along the slope path 836-R of first or right side slope 830-R between upper wall 832-R and lower wall 834-R with bent portion 740-RB of bent trigger shaft 740-R extending through first or right trigger switch slot 836-TSR. Middle plate 400 has an aligned trigger switch slot 436-TSR along slope path 436-R in the first or right slope 430 between upper wall 432 and a lower wall 434 of middle plate 400.

Similarly, further referring to FIG. 7, the front surface 502 of front plate 500 includes a second or left transverse slope 810-L in line with the second or left trap door 600-TDL and offset to a second or left slide slope 830-L having an upper wall 832-L and a lower wall 834-L separated by a distance "D-6" and terminating in a second or left portion of a central end 838-L.

A second or left trigger switch slot 836-TSL is centered along the slope path 836-L of second or left side slope 830-L between upper wall 832-L and lower wall 834-L with bent portion 740-LB of bent trigger shaft 740-L extending through second or left trigger switch slot 836-TSL. Middle plate 400 has an aligned trigger switch slot 436-TSL along slope path 436-L in the second or left slope 430-L between upper wall 432-L and a lower wall 434-L of middle plate 400.

Similarly, front surface 502 of front plate 500 includes a second or left transverse slope 810-L in line with the second or left trap door 600-TDL and offset to a second or left side slope 830-L having an upper wall 832-L and a lower wall 834-L separated by a distance "D-6" and terminating in a second or left portion of a central end 838-L. A second or left trigger switch slot 836-TSL is centered along the slope path 836-L of second or left side slope 830-L between upper wall 832-L and lower wall 834-L with the bent portion 740-LB of bent trigger shaft 740-L extending through second or left trigger switch slot 836-TSL. Middle plate 400 has an aligned trigger switch slot 436-TSL along slope path 436-L in the second or left slope 430-L between upper wall 452 and lower wall 454 of middle plate 400.

Figure 9:
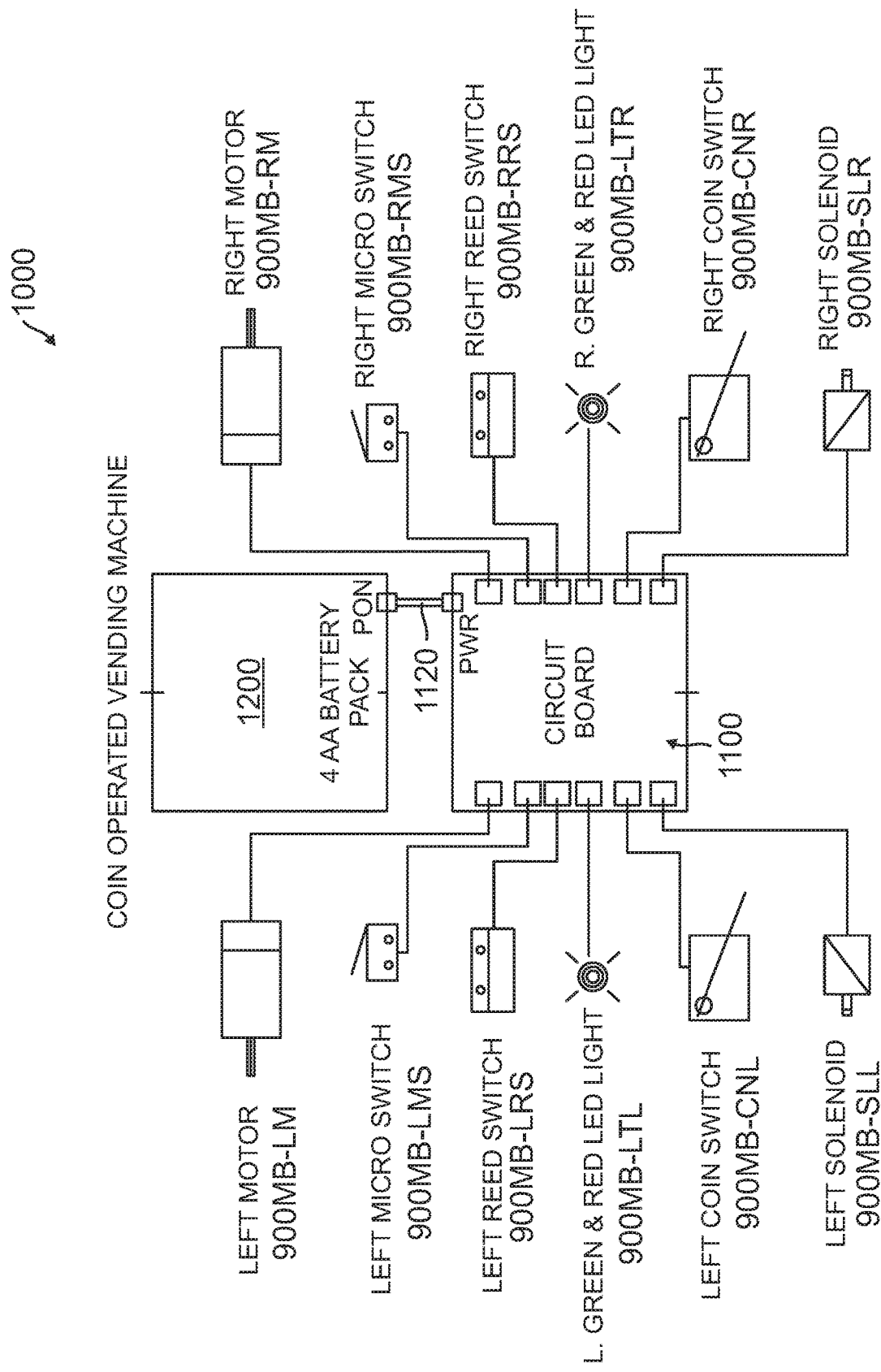
FIG. 9 is a diagram of the motherboard and power supply.

Referring to FIG. 9, there is illustrated a circuit diagram 1000 of connections to a programmed motherboard chip 1100 connected to a source of power 1200, which by way of example is a battery pack including four (4) "AA" batteries. It will be appreciated that it is within the spirit and scope of the present invention to replace the above-described battery pack with any other type or types of batteries or direct electricity for direct 120 volt current or reduced to DC low voltage through a transformer.

For purposes of the innovative coin operation of the present invention, the connections on the motherboard chip 1100 that are used include six (6) for the first or right coin plate assemblies and six (6)) for the second or left coin plate assemblies. For the first or right assembly used to dispense a row of products such as tampons: (I) one lead 900MB-SLR from the first or right trigger switch 700-R is for activation of the first or right solenoid 670-R; (ii) a second lead 900MB-CNR for the first or right coin deposit slot 130 used with right motor lead 900MB-RM and right microswitch lead 900MB-RMS and (iii) one lead 900MB-LTR for a green and red signal light right reed switch 900MB-RMS for the first row of products. For the second or left assembly used to dispense a row of products such as feminine napkins: (i) one lead 900MB-SLL from the second or left trigger switch 700-L is for activation of the second or left solenoid 670-L; (ii) a second lead 900MB-CNL for the second or left coin deposit slot 140 used with left motor lead 900MB-LM and left microswitch lead 900MB-LMS and (iii) one lead 900MB-LTL for a green and red signal light used left reed switch 900MB-LRS for the second row of products.

Figure 10:
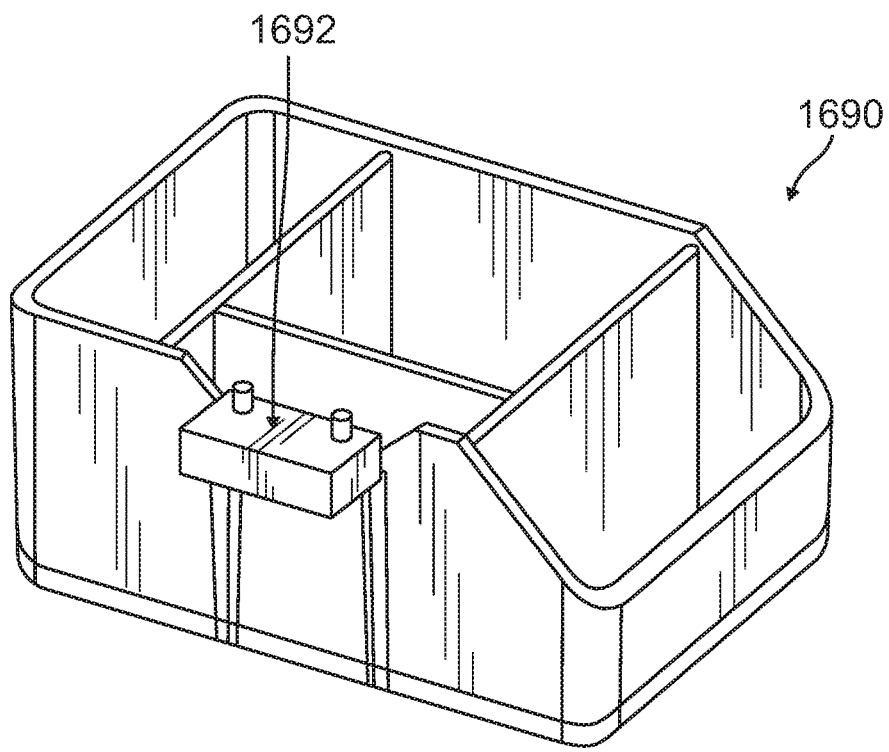
FIG. 10 is an enlarged perspective view of the feminine napkin weight and the feminine napkin magnet on top of the feminine napkin weight.

Referring to FIG. 10, there is illustrated an enlarged perspective view of the feminine napkin weight 1690 and the feminine napkin magnet 1692 on top of the feminine napkin weight 1690.

Figure 11:
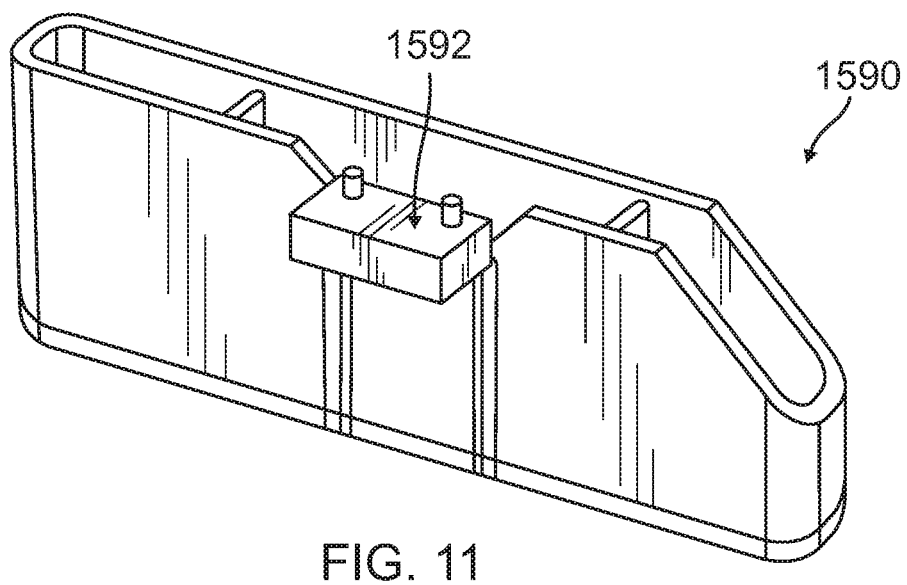
FIG. 11 is an enlarged perspective view of the tampon weight and the tampon magnet on top of the tampon weight.

Referring to FIG. 11, there illustrated an enlarged perspective view of the tampon weight 1590 and the tampon magnet 1592 on top of the tampon weight 1590.

Figure 12:
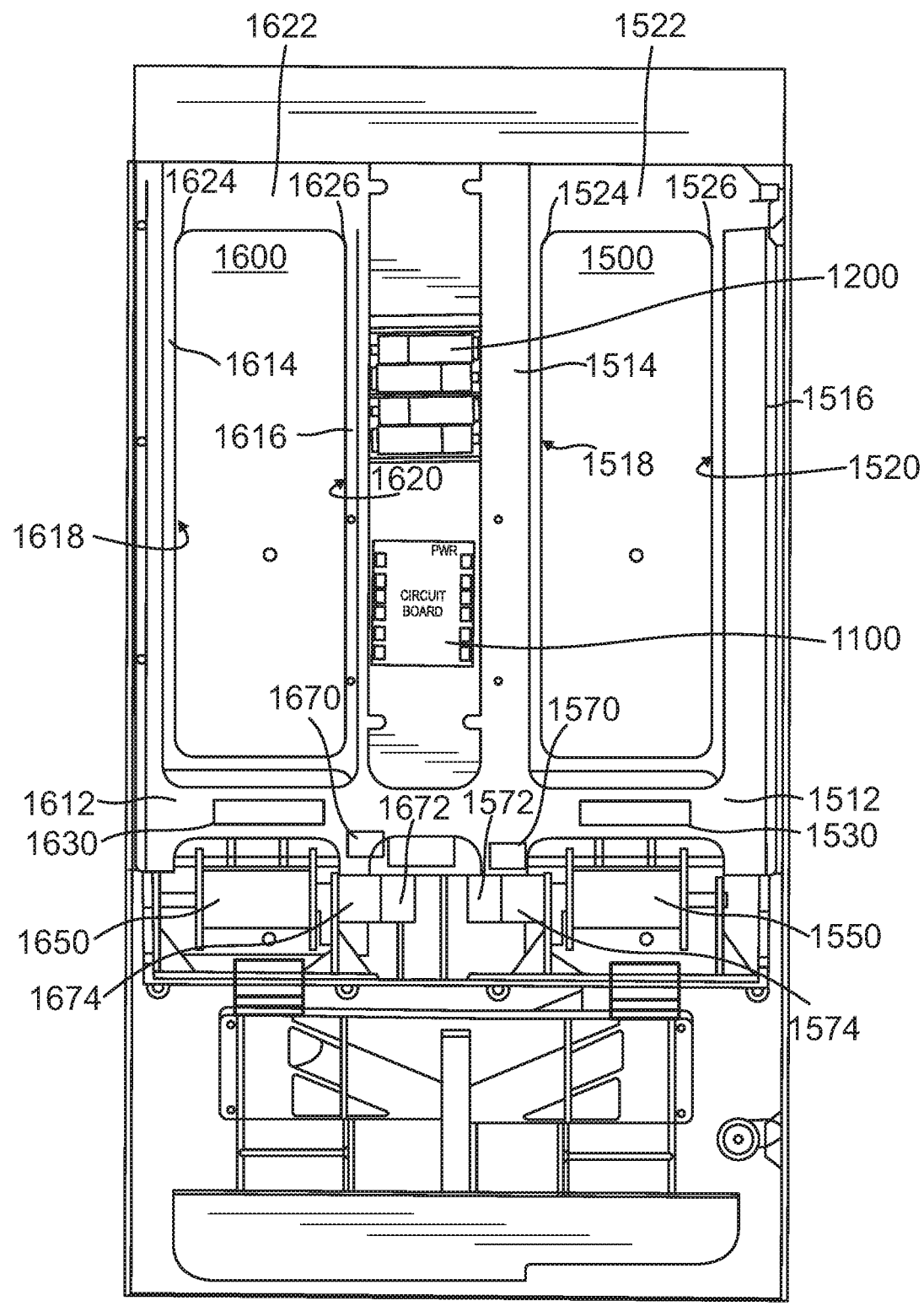
FIG. 12 is a front perspective view of the empty feminine napkin rack on the left and th empty tampon rack on the right, a left feminine napkin dispensing cradle, a left feminine napkin motor, a left feminine napkin shaft, a left feminine napkin microswitch and a left feminine napkin reed switch, and a right tampon dispensing cradle, a right tampon motor, a right tampon shaft, a right tampon microswitch and a right tampon reed switch.

Referring to FIG. 12, there is illustrated a front perspective view when viewed with the front door removed and looking into the body of the vending machine 10 with both the tampon retaining rack and the feminine napkin retaining rack illustrated empty to better illustrate the components of each rack. The tampon retaining rack 1500 is on the right side and includes a tampon lower front wall 1512, a tampon left front wall 1514, a tampon right front wall 1516, a tampon left sidewall 1518, a tampon right sidewall 1520, a tampon upper rear wall 1522, a tampon left rear wall 1524 and a tampon right rear wall 1526. Also illustrated is a tampon reed switch 1530 on the right lower front wall 1512 and a tampon dispensing cradle 1550 which will be described in more detail in FIG. 14. Also illustrated are the tampon right microswitch 1570, the tampon right motor 1572 and the tampon shaft 1574.

Also referring to FIG. 12, there is illustrated the front perspective view of the feminine napkin retaining rack. The feminine napkin retaining rack 1600 is on the left side and includes a feminine napkin lower front wall 1612, a feminine napkin left front wall 1614, a feminine napkin right front wall 1616, a feminine napkin left sidewall 1618, a feminine napkin right sidewall 1620, a feminine napkin upper rear wall 1622, a feminine napkin left rear wall 1624 and a feminine napkin right rear wall 1626. Also illustrated are a feminine napkin reed switch 1630 on the left lower front wall 1612 and a feminine napkin dispensing cradle 1650 which will be described in more detail in FIG. 12. Also illustrated is the feminine napkin left microswitch 1670, the feminine napkin right motor 1672 and the feminine napkin shaft 1674.

Figure 13:
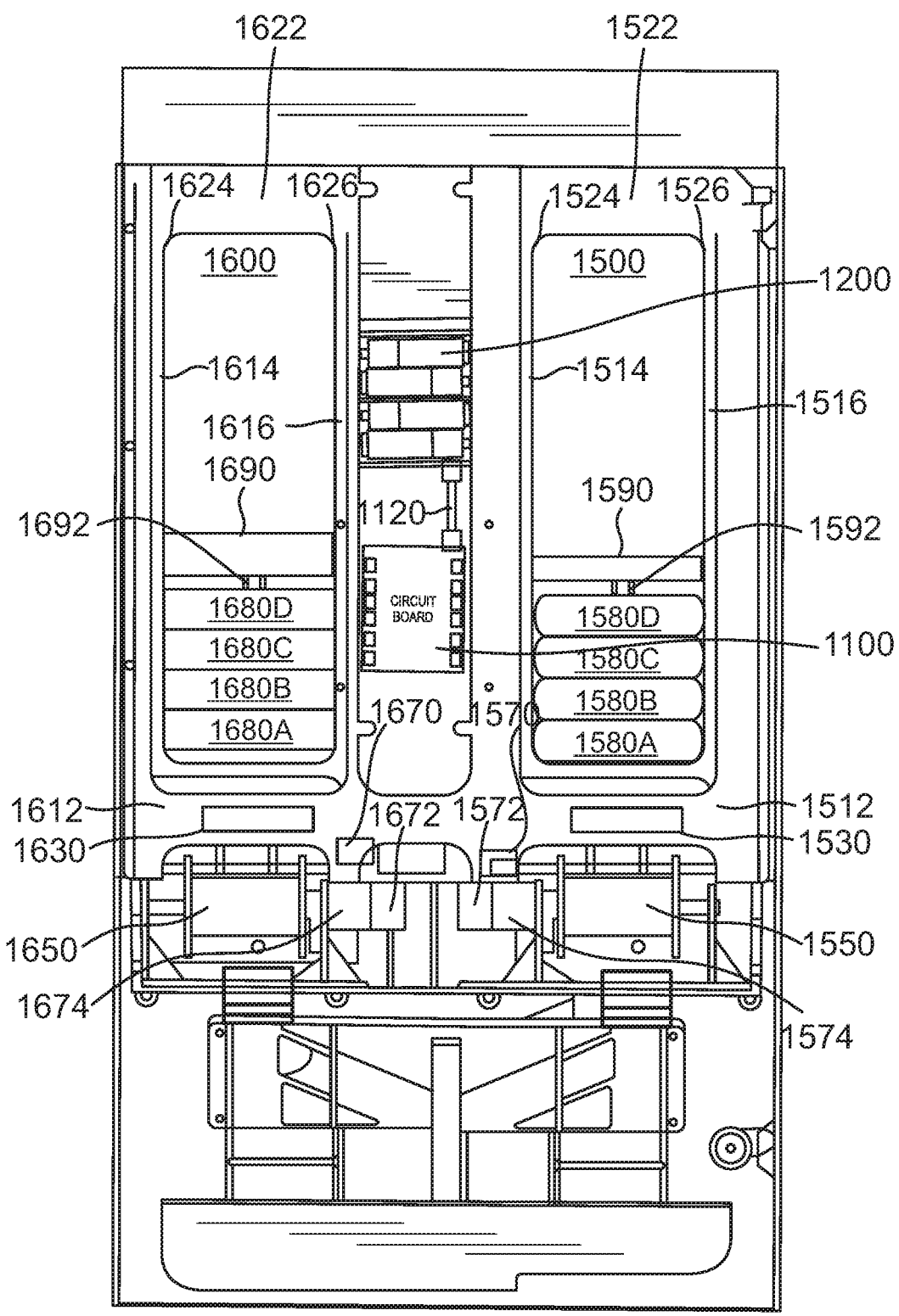
FIG. 13 is a front perspective view of the feminine napkin rack filled with feminine napkins on the left and tampon rack filled with tampons on the right, with a feminine napkin weight and magnet on top of the weight and tampon weight and magnet on top of the weight.

Referring to FIG. 13, there is illustrated the same view as from FIG. 12 but with the tampon rack and the feminine napkin rack filled with tampons and feminine napkins. The tampon retaining rack 1500 has individual tampons 1580A, 1580B, 1580C and 1580D in a row of tampons, a weight 1590 on the uppermost tampon 1580D and a tampon magnet 1592 on weight 1590. On the left side, the feminine napkin retaining rack 1600 has individual feminine napkins 1680A, 1680B, 1680C and 1680D an a row of feminine napkins, a weight 1690 on uppermost feminine napkin 1680D and a feminine napkin magnet 1692 on weight 1690.

Figure 14:
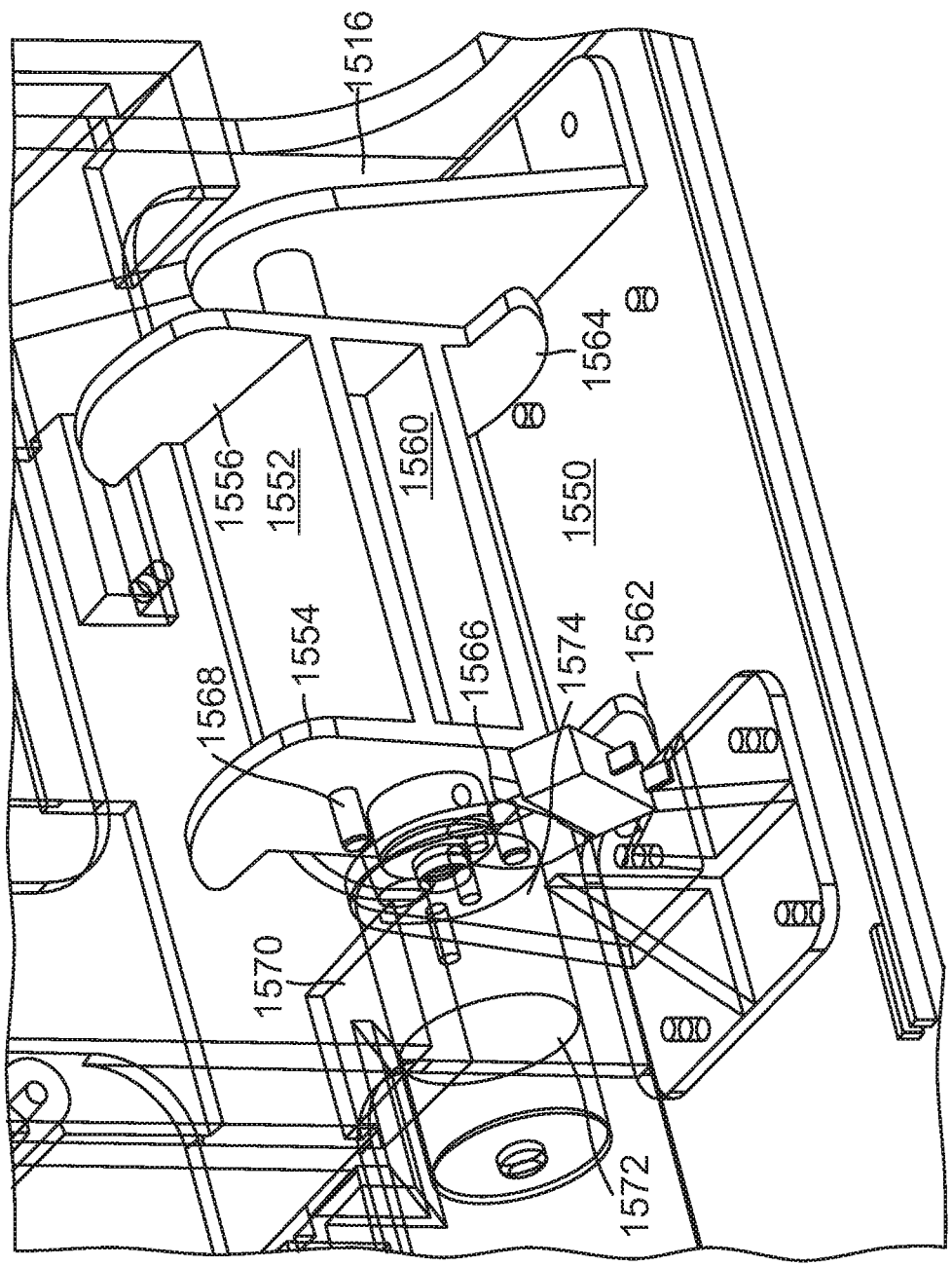
FIG. 14 is an enlarged perspective view of the tampon dispensing cradle, the tampon motor, the tampon shaft, the tampon microswitch and the pin from the tampon cradle.

Referring to FIG. 14, there is illustrated a detailed view of the tampon dispensing cradle 1550 which includes an upper platform 1552, an upper left arm 1554 and an upper right arm 1556 and a tampon pin 1568. Also illustrated is a lower platform 1560, the lower left arm 1562 and the lower right arm 1564 and the lower pin 1566. When the proper coins are inserted as previously described and there is a sufficient quantity of tampon in the rack, the lowermost tampon 1580A is dispensed into the upper platform 1552 of the tampon dispensing cradle 1550 and the tampon motor 1572 rotates the tampon shaft 1574 until the tampon pin 1568 comes in contact with the tampon microswitch 1570 which causes the motor to stop rotating and the lowermost product is now dispensed into the retaining opening 150 for a retaining shelf 152 wherein the retrieved tray 152 where the tampon is retrieved.

Figure 15:
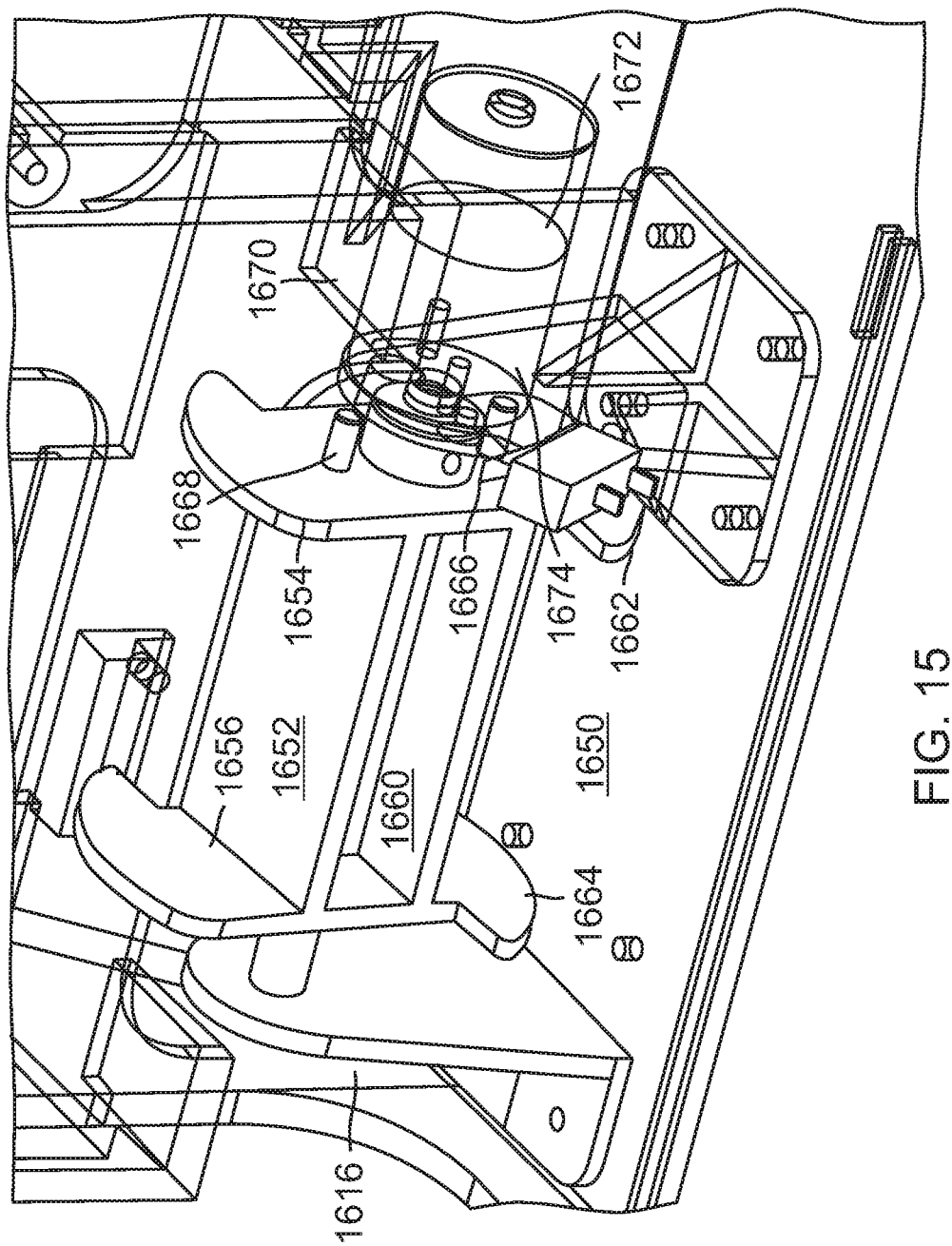
FIG. 15 is a feminine napkin dispensing cradle, the feminine napkin motor, the feminine napkin shaft, the feminine napkin microswitch and the pin from the feminine napkin cradle.

Similarly, referring to FIG. 15, for the feminine napkin retaining rack, there is illustrated a detailed view of the feminine napkin dispensing cradle 1650 which includes an upper platform 1652, an upper left arm 1654 and an upper right arm 1656 and a feminine napkin pin 1668. Also illustrated is a lower platform 1660, the lower left arm 1662 and the lower right arm 1664 and the lower pin 1666. When the proper coins are inserted as previously described and there is a sufficient quantity of feminine napkin in the rack, the lowermost feminine napkin 1680A is dispensed into the upper platform 1652 of the feminine napkin dispensing cradle 1650 and the feminine napkin motor 1672 rotates the feminine napkin shaft 1674 until the feminine napkin pin 1668 comes in contact with the feminine napkin microswitch 1670 which causes the motor to stop rotating and the lowermost product is now dispensed into the retaining tray 152 where the feminine napkin is retrieved.

Figure 16:
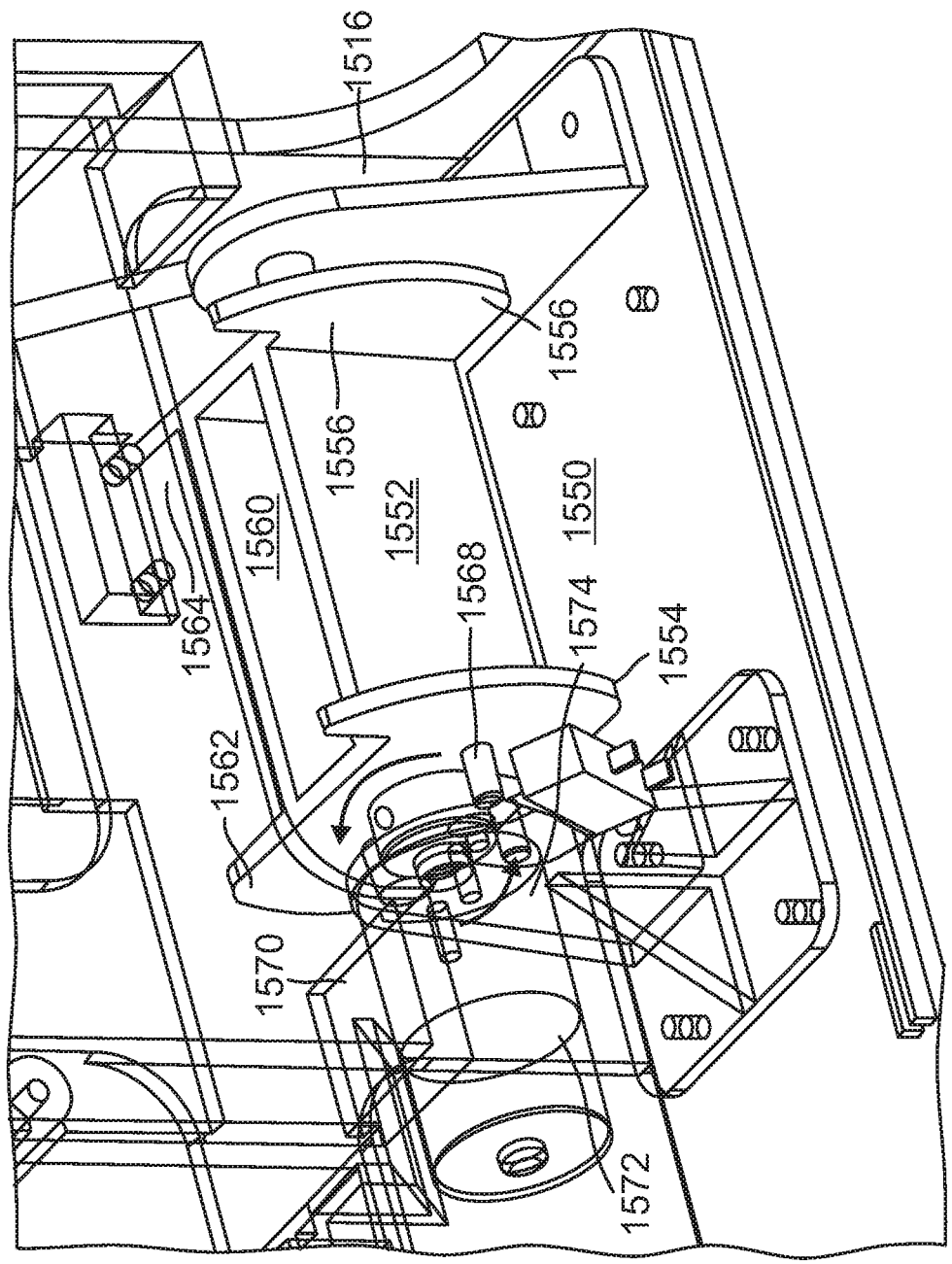
FIG. 16 is an enlarged perspective view of the tampon dispensing cradle, the tampon motor, the tampon shaft, the tampon microswitch and the pin from the tampon cradle, illustrating the cradle in an operative mode to dispense a product such as a tampon.

Referring to FIG. 16, there is illustrated an enlarged perspective view of the tampon dispensing cradle, the tampon motor, the tampon shaft, the tampon microswitch and the pin from the tampon cradle, illustrating the cradle in an operative mode to dispense a product such as a tampon. The part numbers are the same as identified in FIG. 14.

Also referring to FIGS. 12 and 13, in the center separate compartment 1100 between the tampon rack 1500 and the feminine rack 1600 is a compartment wall 1120 retaining the motherboard 1000 and the power pack 1200. An electrical connector connected the motherboard 1100 to the power bank 1200.

The operation of the vending machine 100 will now be discussed. As previously stated, if an improper coin such as a penny, nickle or dime is inserted into first or right coin deposit slot 130 (as identified from the rear surface 120), the coin is guided along first or right transverse slope 310-R to the first or right coin return plate 340-R which causes the improperly inserted coin to fall into the retrieval tray 152 to be retrieved by the person who inserted the wrong coin. Similarly, if an improper coin such as a penny, nickle or dime is inserted into second or left coin deposit slot 140 (as identified from the rear surface 120), the coin is guided along second or left transverse slope 350-L to the second or left coin return plate 360-L which causes the improperly inserted coin to fall into the retrieval tray 152 to be retrieved by the person who inserted the wrong coin.

By way of example, the motherboard 1100 is pre-programmed for the vending machine to accept quarters as the proper coin. The motherboard 1100 is pre-programmed for either one quarter or two quarters as the price of a product, which usually is either a tampon or a feminine napkin. If a correct coin, using one quarter as an example, is inserted into coin slot 130 for the purchase of a tampon 1580A and the column 1500 does have at least one tampon available for sale, the quarter 5000 is guided along right slop 830-R of front plate 5000 as illustrated in FIG. 7, is guided between upper wall 832-R and lower wall 834-R until it reaches central end portion 838-R as the quarter rolls down along slope path 836-R, the quarter 5000 hits the bent portion 740-RB of bent trigger shaft 740-R of right trigger switch 700-R and falls into locked coin box 6000. Concurrently, the lowermost tampon 1580A falls onto upper platform 1552 of tampon dispensing cradle 1550 and the motherboard causes right tampon motor 1572 to rotate so that shaft 1574 rotates and tampon dispensing cradle 1550 rotates until upper platform 1552 is upside down, the tampon 1580A falls onto the retrieval tray 1552 and the upper tampon pin 1568 contact tampon microswitch 1570 which causes the right tampon motor 1572 to stop.

Similarly, if a correct coin, using one quarter as an example, is inserted into coin slot 140 for the purchase of a feminine napkin 1680A and the column 1600 does have at least one feminine napkin available for sale, the quarter 5000 is guided to roll along left slid e slope 830-L of front plate 500 as illustrated in FIG. 7, is guided between upper wall 832-L and lower wall 834-L until it reachers central end portion 838-L as the quarter rolls down along slope path 836-L, the quarter 5000 hits the bent portion 740-LB of bent trigger shaft 740-1 of LEFT trigger switch 700-1 and falls into locked coin box 6000. Concurrently, the lowermost feminine napkin 1680A falls onto upper platform 1652 of feminine napkin dispensing cradle 1650 and the motherboard causes left feminine napkin motor 1672 to rotate so that shaft 1674 rotates and the feminine napkin dispensing cradle 1650 rotates until upper platform 1652 is upside down, the feminine napkin 1680A falls onto the retrieval tray 1652 and the upper feminine napkin pin 1668 contacts feminine napkin microswitch 1670 which causes the left feminine napkin motor 156 to stop.

If the supply of a product is exhausted and there is no more product in a rack, an out-of-product warning light advises a potential purchaser not to purchase the product. If the tampon rack 1500 is out of tampons 1580, the tampon weight 1590 is at the bottom of the tampon column and the tampon magnet 1592 is in communication distance with the tampon reed switch 1592.

The motherboard 1100 receives an out-of-product signal from the right reed switch 1530 and causes a warning light, which by way of example is a red blinking light, to shine through opening 132. Similarly, if the feminine napkin rack 1600 is out of feminine napkins 1680, the feminine napkin weight 1690 is at the bottom of the feminine napkin column and the feminine napkin magnet is in communication distance with the feminine napkin reed switch 1630. The motherboard 1100 receives an out-of-product signal from the left reed switch 1630 and causes a warning light, which by way of example, is a red blinking light, to shine through opening 142.

If a purchaser does not see the out-of-product signal or ignores it and deposits the correct coin 500 in the correct slot 130, the following occurs. The bent portion 740-RB of bent trigger shaft 740-R of right trigger switch 700-R extends through right trigger switch slot 836-TSR in right slide slope 830-R of front plate 500 and through trigger switch slot 436-R along right slide slope 436-R of the middle plate 400 and the rolling quarter rolling along either right slide slope.

If middle plate 400 or right slide slope 838-R in front plate 500 hits the bent portion 740-RB of right trigger shaft 740-R, this causes a signal from the motherboard 1100 to activate the right solenoid 670-R causes the retaining pin to move from its restraining contact against right trap door plate 610-R to move into the right solenoid 670-Ra. The under tension spring force of tampon force spring 619-R causes spring loaded right trap door 600-TDR to rotate in a counter-clockwise direction, to rotate from the front surface 502 of third or front plate 500, thereby exposing a right trap door opening 500-TDOR which is aligned with the right trap door opening of middle plate 400, thereby causing the quarter 5000 to fall through either trap door opening and onto the upper surface 344 of return plate 344-R and onto retrieval tray 152.

Similarly, if a purchaser does not see the out-of-product signal or ignores it and deposits the correct coin 5000 in the correct slot 140, the following occurs. The bent portion 740-LB of bent trigger shaft 740-L of left trigger switch 700-L extends through left trigger switch slot 836-TSL in left slide slope 830-L of front plate 500 and through trigger switch slot 436-L along left slide slope 436-L of middle plate 400 and the rolling quarter rolling along either left slide slope.

If middle plate 400 or left slide slope 838-L in front plate 500 hits the bent portion 740-RL of left trigger shaft 740-L, this causes a signal from the motherboard 1100 to activate the left solenoid 670-L causing the retaining pin to move from its restraining condition against left trap door plate 610-L to move back into the left solenoid 670-L. The under tension spring force of feminine napkin force spring 619-L causes spring loaded left trap door 600-TDL to rotate in a clockwise direction, to rotate away from the front surface 502 of third or front plate 500 thereby exposing a left trap door opening 500-TDOL which is aligned with the left trap door opening of middle plate 400, thereby causing the quarter 5000 to fall through either trap door opening and onto the upper surface 364 of return plate 360-L 44 of return plate 344-R and onto retrieval tray 152.

Of course the present invention is not intended to be restricted to any particular form or arrangement, or any specific embodiment, or any specific use, disclosed herein, since the same may be modified in various particulars or relations without departing from the spirit or scope of the claimed invention herein above shown and described of which the apparatus or method shown is intended only for illustration and disclosure of an operative embodiment and not to show all of the various forms or modifications in which this invention might be embodied or operated.

What is claimed is:

1. An apparatus for dispensing a first product and a second product, the apparatus comprising:
   (a) a cabinet with a front door including a first product coin deposit slot and a spaced apart second product coin deposit slot, a retrieval opening leading to a retrieval tray;
   (b) a back plate including a rear surface facing a back surface of the cabinet front door, the back plate having a front surface including a first transverse slope extending from adjacent the first coin deposit slot and in line with a first coin return plate, a first slide slope extending from adjacent an upper portion of the first transverse slope and extending to a first portion of a central end;
   (c) said front surface of said back plate further including a second transverse slope extending from adjacent the second coin deposit slot and in line with a second coin return plate, a second slide slope extending from adjacent an upper portion of the second transverse slope and extending to a second portion of a central end, a first middle trigger switch slot centered along a slope path of a first middle slide slope,
   (d) a middle plate including a back surface facing said front surface of said back plate, the middle plate having a front surface including a first middle transverse slope in line with a first middle trap door opening and offset to a first middle slide slope having an upper wall and a lower wall terminating in a first middle portion of a central end, a first middle trigger switch slot centered along a slope path of the first middle slide slope;
   (e) said front of said middle plate further including a second middle transverse slope in line with a second middle trap door opening and offset to a second middle slide slope having an upper wall and a lower wall terminating in a second middle portion of a central end, a second middle trigger switch slot centered along a slope path of the second middle slide slope,
   (f) a front plate including a back surface facing said front surface of said middle plate, the front plate having a front surface including the following operating components:
      (i) a first spring loaded trap door including a first force spring affixed to the first spring loaded trap door, a first solenoid affixed to the front surface of the front plate, the first solenoid having a first retaining pin retained against the first spring loaded trap door to prevent the first force spring from exerting a counterclockwise opening force on the first spring loaded trap door;
      (ii) a second spring loaded trap door including a second force spring affixed to the second spring loaded trap door, a second solenoid affixed to the front surface of the front plate, the second solenoid having a second retaining pin retained against the second spring loaded trap door to prevent the second force spring from exerting a clockwise opening force on the second spring loaded trap door;
      (iii) the front plate front surface including a first front transverse slope in line with the first spring loaded trap door and offset to a first front slide slope terminating in a first front portion of a central end leading to a coin collection box, a first front trigger switch slot centered along a slope path of the first slide slope, a first trigger switch with a trigger shaft including at least a right bent portion extending through both the first front trigger switch slot and the first middle trigger switch slot;
      (iv) the front plate front surface including a second front transverse slope in line with the second spring loaded trap door and offset to a second front slide slope terminating in a second front portion of a central end leading to a coin collection box, a second front trigger switch slot centered along a slope path of the second slide slope, a second trigger switch with a trigger shaft including at least a second bent portion extending through both the second front trigger switch slot and the second middle trigger switch slot;
   (g) a first product rail retaining a column of individual first products, a first reed switch adjacent a bottom of said first column, a first product weight bearing platform resting on an uppermost individual first product, the first weight bearing platform retaining a first magnet, a first product dispensing cradle having at least a platform to receive a lowermost first product, a first product motor rotatably affixed to the first cradle, a first microswitch affixed adjacent the first product dispensing cradle, at least a transverse first pin affixed to the first cradle and positioned for contact with the first microswitch; and
   (h) a second product rail retaining a column of individual second products, a second reed switch adjacent a bottom of said second column, a second product weight bearing platform resting on an uppermost individual second product, the second weight bearing platform retaining a second magnet, a second product dispensing cradle having at least a platform to receive a lowermost second product, a second product motor rotatably affixed to the second cradle, a second microswitch affixed adjacent the second product dispensing cradle, at least a transverse second pin affixed to the second cradle and positioned for contact with the second microswitch.

2. The apparatus for dispensing a first product and a second product in accordance with claim 1, the apparatus further comprising: a programed motherboard connected to a source of power, the programmed motherboard having a multiplicity of connections including:
 (a) a lead for a right trigger switch is for activation of a right solenoid;
 (b) a second lead for the right coin deposit slot used with a right motor lead and a right microswitch lead
 (c) a lead for a right reed switch for a tampon out-of-product signal light;
 (d) a lead for a left trigger switch for activation of a left solenoid;
 (e) a second lead for the left coin deposit slot used with a left motor lead and a left microswitch lead; and
 (f) a lead for a left reed switch for a feminine napkin out-of-product signal light.

3. The apparatus for dispensing a first product and a second product in accordance with claim 2, further comprising:
 a mounting plate with an upper surface retained against the back surface of the back wall of the front door, the mounting plate and the back plate retained against the back wall by a right mounting bracket and a left mounting bracket, a bottom surface of the right coin return plate affixed to the separation plate and a bottom surface of the left coin return plate affixed to the separation plate.

4. The apparatus for dispensing a first product and a second product in accordance with claim 3, further comprising:
 the middle plate including a first rear end affixed to a first front end of the rear plate, the middle plate including a second rear end affixed to a second front end of the rear plate, a first front end of the front plate is affixed to a first rear end of the middle plant and a second front end of the front plate is affixed to a second rear end of the middle plate.

5. The apparatus for dispensing a first product and a second product in accordance with claim 2, further comprising:
 said first product is a multiplicity of individual tampons and said first product rail further comprises a right tampon rail having a first right upper back wall including a first right longitudinal back wall leading to a first right longitudinal side wall leading to a first right longitudinal front wall and a second right longitudinal back wall leading to a second right longitudinal side wall leading to a second right longitudinal front wall, a right lower front wall retaining said first reed switch, the right tampon rail configured to retain a column of individual tampons, said right top weight bearing platform resting on an uppermost tampon.

6. The apparatus for dispensing a first product and a second product in accordance with claim 5 further comprising:
 said second product is a multiplicity of individual feminine napkins and said second product rail further comprises a left feminine napkin rail having a first left upper back wall including a first left longitudinal back wall leading to a first left longitudinal side wall leading to a first left longitudinal front wall and a second right longitudinal back wall leading to a second right longitudinal side wall leading to a second right longitudinal front wall, a left lower front wall retaining the second reed switch, the left feminine napkin rail configured to retain a column of individual feminine napkins, the second top weight bearing platform resting on an uppermost feminine napkin.

7. The apparatus for dispensing a first product and a second product in accordance with claim 6 further comprising:
 said first dispensing cradle is a tampon dispensing cradle including a tampon upper platform, an upper left arm an upper right arm and an upper tampon pin, a lower tampon platform, a lower left arm, a lower right arm and a lower tampon pin, a right tampon motor connected to a right motor shaft connected to the right tampon cradle, a tampon microswitch affixed adjacent the left upper arm and in contact with both the upper tampon pin and the lower tampon pin.

8. The apparatus for dispensing a first product and a second product in accordance with claim 7 further comprising:
 said second dispensing cradle is a feminine napkin dispensing cradle including a feminine napkin upper platform, an upper left arm an upper right arm and an upper feminine napkin pin, a lower feminine napkin platform, a lower left arm, a lower right arm and a lower feminine napkin pin, a left feminine napkin motor connected to a left motor shaft connected to the left feminine napkin cradle, a feminine napkin microswitch affixed adjacent the left upper arm and in contact with both.

9. The apparatus for dispensing a first product and a second product in accordance with claim 8 further comprising:
 (a) if an improper coin such as a penny, nickle or dime is inserted into first coin deposit slot, the coin is guided along the first transverse slope to the first coin return plate which causes the improperly inserted coin to fall into the retrieval tray; and
 (b) if an improper coin such as a penny, nickle or dime is inserted into the second coin deposit slot, the coin is guided along the second transverse slope to the second coin return plate which causes the improperly inserted coin to fall into the retrieval tray.

10. The apparatus for dispensing a first product and a second product in accordance with claim 8 further comprising:
 (a) said motherboard is pre-programmed for the apparatus to accept at least one quarter as the proper coin for the purchase of an individual tampon and the tampon column has at least one individual tampon available for sale, the at least one quarter is guided between the front upper wall and lower wall of the first front slide slope terminating in a first front portion of a central end leading to a coin collection box until the at least one quarter reaches the central end portion as the quarter rolls down along the first front slide slope path, the at least one quarter hits the bent portion of bent trigger shaft of first trigger switch and falls into locked coin box;
 (b) concurrently, a lowermost tampon falls onto the upper platform of the tampon dispensing cradle and the motherboard causes the first tampon motor to turn on so that a first tampon motor shaft connected to the first tampon motor and the tampon dispensing cradle rotates and tampon dispensing cradle rotates until the tampon dispensing cradle upper platform is upside down, the lowermost tampon falls onto the retrieval tray and the upper tampon pin contacts the tampon microswitch which causes the first tampon motor to stop.

11. The apparatus for dispensing a first product and a second product in accordance with claim 8 further comprising:
   (a) said motherboard is pre-programmed for the apparatus to accept at least one quarter as the proper coin for purchase of an individual feminine napkin and the feminine napkin column has at least one individual feminine napkin available for sale, the at least one quarter is guided between the front upper wall and lower wall of the second front slide slope terminating in a second front portion of a central end leading to a coin collection box until the at least one quarter reaches the central end portion as the quarter rolls down along the second front slide slope path, the at least one quarter hits the bent portion of bent trigger shaft of second trigger switch and falls into locked coin box;
   (b) concurrently, a lowermost feminine napkin falls onto the upper platform of the feminine napkin dispensing cradle and the motherboard causes the first feminine napkin motor to turn on so that a first feminine napkin motor shaft connected to the first feminine napkin motor and the feminine napkin dispensing cradle rotates and feminine napkin dispensing cradle rotates until the feminine napkin dispensing cradle upper platform is upside down, the lowermost feminine napkin falls onto the retrieval tray and the upper feminine napkin pin contacts the feminine napkin microswitch which causes the first feminine napkin motor to stop.

12. The apparatus for dispensing a first product and a second product in accordance with claim 8 further comprising:
   a supply of a product is exhausted and there is no more product in a rack, an out-of-product warning light advises a potential purchaser not to purchase the product.

13. The apparatus for dispensing a first product and a second product in accordance with claim 8 further comprising:
   (a) if the tampon rack is out of tampons, the tampon weight is at the bottom of the tampon column and the tampon magnet is in communication distance with the first tampon reed switch; and
   (b) the motherboard receives an out-of-product signal from the first tampon reed switch and causes a warning light to shine through an opening in the front door adjacent the tampon slot.

14. The apparatus for dispensing a first product and a second product in accordance with claim 8 further comprising:
   (a) if the feminine napkin rack is out of feminine napkins, the feminine napkin weight is at the bottom of the feminine napkin column and the feminine napkin magnet is in communication distance with the first feminine napkin reed switch; and
   (b) the motherboard receives an out-of-product signal from the first feminine napkin reed switch and causes a warning light to shine through an opening in the front door adjacent the feminine napkin slot.

15. The apparatus for dispensing a first product and a second product in accordance with claim 8 further comprising:
   (a) said motherboard is pre-programmed for the apparatus to accept at least one quarter as the proper coin for the purchase of an individual tampon but the tampon column is out of tampons and the at least one quarter is inserted into the tampon slot; and
   (b) the bent portion of bent trigger shaft of first trigger switch extends through first front trigger switch slot in first front slide slope of the front plate and through the trigger switch slot along first middle slide slope of the middle plate and a rolling at least one quarter rolls along either the first middle slide slope in the middle plate or along first front slide slope in the front plate and hits the bent portion of first trigger shaft which causes a signal from the motherboard to activate the right solenoid causes the first retaining pin to move from its restraining contact against first spring load trap door plate to move into a first solenoid so that first force spring under the tension spring force of tampon force spring causes the first spring loaded trap door to rotate in a counter-clockwise direction, to rotate from the front surface of the front plate to thereby exposing a front plate right trap door opening which is aligned with a right trap door opening of middle plate, thereby causing the at least one quarter to fall through either trap door opening and onto the upper surface of the first return plate and onto the retrieval tray.

16. The apparatus for dispensing a first product and a second product in accordance with claim 8 further comprising:
   (a) said motherboard is pre-programmed for the apparatus to accept at least one quarter as the proper coin for the purchase of an individual feminine napkin but the feminine napkin column is out of feminine napkins and the at least one quarter is inserted into the feminine napkin slot; and
   (b) the bent portion of bent trigger shaft of second trigger switch extends through second front trigger switch slot in second front slide slope of the front plate and through the trigger switch slot along second middle slide slope of the middle plate and a rolling at least one quarter rolls along either the second middle slide slope in the middle plate or along second front slide slope in the front plate and hits the bent portion of second trigger shaft which causes a signal from the motherboard to activate a left solenoid causes the second retaining pin to move from its restraining contact against second spring loaded trap door plate to move into the second solenoid so that second force spring under the tension spring force of feminine napkin force spring causes the second spring loaded trap door to rotate in a clockwise direction, to rotate from the front surface of the front plate to thereby exposing a front plate left trap door opening which is aligned with a left trap door opening of middle plate, thereby causing the at least one quarter to fall through either trap door opening and onto the upper surface of the second return plate and onto the retrieval tray.

17. An apparatus for dispensing feminine napkins and tampons, the apparatus comprising:
   (a) a cabinet with a rotatably attached front door including a first coin deposit and a spaced apart second coin deposit slot, a retrieval opening leading to a retrieval tray;
   (b) a back plate including a rear surface facing a back surface of front cabinet door, a front surface including right transverse slope in line with a right coin return plate, a right coin slide slope extending from adjacent an upper portion of the right transverse slope and extending to a right portion of a central end with the right con slide slope having a right upper wall and a right lower wall separated by a first distance sized to receive a quarter, a first right trap door opening aligned with the right coin return plate;

(c) said front surface of said back plate further including a left transverse slope in line with a left coin return plate, a left coin slide slope extending from adjacent an upper portion of the left transverse slope and extending to a left portion of a central end with the left coin slide slope having a left upper wall and a left lower wall separated by a second distance sized to receive a quarter, a first left trap door opening aligned with the let coin return plate;

(d) a middle plate including a back surface facing said front surface of said back plate, the middle plate having a front surface including a right transverse slope in line with a right trap door opening and offset to a right slide slope having an upper wall and a lower wall separated by a third distance and terminating in a right portion of a central end;

(e) said front of said middle plate further including a left transverse slope in line with a left trap door opening and offset to a left slide slope having an upper wall and a lower wall separated by a fourth distance and terminating in a left portion of a central end;

(f) a front plate including a back surface facing said front surface of said middle plate, the front plate having a front surface including the following operating:

(i) a spring loaded right trap door including a right plate with a rear surface including with a first pair of spaced part arms including a first arm having a central opening and a spaced apart second arm with a central opening, a right return spring with a first bent post inserted into the central opening of the first arm and a second bent post inserted into the central opening of second arm, each bent post respectively terminating in a first spring coil and second spring coil respectively wrapped around a retaining post, the first spring coil extends to a first interior shaft and the second spring coil tends to a second interior shaft, respective distal ends of the first and second interior shafts join into a transverse shaft retained in spring tension against right spring plate;

(ii) a right solenoid affixed to the front surface of front plate the right solenoid having a right retaining pin retained against the right trap door;

(iii) a spring loaded left trap door including a left plate with a rear surface including a second pair of spaced part arms including a first arm having a central opening and a spaced apart second arm with a central opening, a left return spring with a first bent post inserted into the central opening of the first arm and a second bent post inserted into the central opening of the second arm, each bent post respectively terminating in a first spring coil and second spring coil respectively wrapped around a retaining post, the first spring coil extends to a first interior shaft and the second spring coil extends to a second interior shaft, respective distal ends of the first and second interior shafts join into a transverse shaft retained in spring tension against left spring plate;

(iv) a left solenoid affixed to the front surface of the front plate, the left solenoid having a left retaining pin retained against the left trap door;

(v) the front plate front surface including a right transverse slope in line with the right spring loaded trap door and offset to a right slide slope having an upper wall and a lower wall separated by a fifth distance and terminating in a right portion of a central end, a right trigger switch slot centered along the right slope path, a right trigger switch with a trigger shaft including at least a right bent portion;

(vi) the front plate front surface further including a left transverse slope in line with the left spring loaded trap door and offset to a left slide slope having an upper wall and a lower wall separated by a sixth distance and terminating in a left portion of a central end, a left trigger switch slot centered along the left slope path, a left trigger switch with a trigger shaft including at least a left bent portion;

(g) a mounting plate with an upper surface retained against the back surface of the back wall of the front door, the mounting plate and the back plate is retained against the back wall by a right mounting bracket and a left mounting bracket, a bottom surface of the right coin return plate affixed to the separation plate and a bottom surface of the left coin return plate affixed to the separation plate, the middle plate including the right rear end is affixed to a right front end of the rear plate, a left rear end of the middle plate is affixed to a left front end of the rear plate, a right front end of the front plate is affixed to a right rear end of the middle plant and a left front end of the front plate is affixed to a left rear end of the middle plate;

(h) said front plate including a right trigger switch slot centered along the right slope path, the middle plate including a right trigger switch slot centered in the right slope path, the right trigger switch slot in the front plate aligned with the right trigger switch slot in the middle plate, said front plate including a left trigger switch slot centered along the left slope path, the middle plate including a left trigger switch slot centered in the left slope path, the left trigger switch slot in the front plate aligned with the left trigger switch slot in the middle plate, (i) a right tampon rail having a first right upper back wall including a first right longitudinal back wall leading to a first right longitudinal side wall leading to a first right longitudinal front wall and a second right longitudinal back wall leading to a second right longitudinal side wall leading to a second right longitudinal front wall, a right lower front wall retaining a right reed switch, the right tampon rail configured to retain a column of individual tampons, a right top weight bearing platform resting on an uppermost tampon, the right weight bearing platform retaining a right magnet;

(j) a left feminine napkin rail having a first left upper back wall including a first left longitudinal back wall leading to a first left longitudinal side wall leading to a first left longitudinal front wall and a second left longitudinal back wall leading to a second right longitudinal side wall leading to a second left longitudinal front wall, a left lower front wall retaining a left reed switch, the left feminine napkin rail configured to retain a column of individual feminine napkins, a left top weight bearing platform resting on an uppermost feminine napkin, the left weight bearing platform retaining a left magnet;

(k) a programed motherboard connected to a source of power, the programmed motherboard having a multiplicity connections including:

(i) a lead for a right trigger switch is for activation of the right solenoid, (ii) a second lead for the right coin deposit slot used with a right motor lead and a right microswitch lead, (iii) a lead for a right reed switch for a tampon out-of-product signal light,
(iv) a lead for a left trigger switch is for activation of the left solenoid,
(v) a second lead for the left coin deposit slot used with a left motor lead and a left microswitch lead,
(vii) a lead for a left reed switch for a feminine napkin out-of-product signal light, (l) a tampon dispensing cradle including a tampon upper platform, an upper left arm an upper right arm and an upper tampon pin, a lower tampon platform, a lower left arm, a lower right arm and a lower tampon pin, a right tampon motor connected to a right motor shaft connected to the right tampon cradle, a tampon microswitch affixed adjacent the left upper arm and in contact with both the upper tampon pin and the lower tampon pin;

(m) a feminine napkin dispensing cradle including a feminine napkin upper platform, an upper left arm an upper right arm and an upper feminine napkin pin, a lower feminine napkin platform, a lower left arm, a lower right arm and a lower feminine napkin pin, a left feminine napkin motor connected to a left motor shaft connected to the left feminine napkin cradle, a feminine napkin microswitch affixed adjacent the left upper arm and in contact with both the upper feminine napkin pin and the lower feminine napkin pin.

* * * * *